United States Patent
Wisniewski et al.

(10) Patent No.: US 10,960,019 B2
(45) Date of Patent: *Mar. 30, 2021

(54) PREVENTING AND TREATING AMYLOID-BETA DEPOSITION BY STIMULATION OF INNATE IMMUNITY

(71) Applicant: NEW YORK UNIVERSITY, New York, NY (US)

(72) Inventors: Thomas Wisniewski, Staten Island, NY (US); Daryl Spinner, Staten Island, NY (US); Henrieta Scholtzova, Fords, NJ (US); Richard Kascsak, Morganville, NJ (US)

(73) Assignee: New York University, New York, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 16/458,966

(22) Filed: Jul. 1, 2019

(65) Prior Publication Data

US 2019/0328764 A1 Oct. 31, 2019

Related U.S. Application Data

(63) Continuation of application No. 12/918,739, filed as application No. PCT/US2009/034677 on Feb. 20, 2009, now Pat. No. 10,383,887.

(60) Provisional application No. 61/030,089, filed on Feb. 20, 2008.

(51) Int. Cl.
| | |
|---|---|
| *A61K 31/7088* | (2006.01) |
| *A61K 39/00* | (2006.01) |
| *A61P 25/28* | (2006.01) |
| *A61K 48/00* | (2006.01) |
| *C12N 15/85* | (2006.01) |
| *C12N 15/117* | (2010.01) |

(52) U.S. Cl.
CPC .......... *A61K 31/7088* (2013.01); *A61K 48/00* (2013.01); *A61P 25/28* (2018.01); *C12N 15/85* (2013.01); *A61K 2039/545* (2013.01); *A61K 2039/55561* (2013.01); *A61K 2039/57* (2013.01); *C12N 15/117* (2013.01)

(58) Field of Classification Search
CPC ...... A61K 31/7088; A61K 2039/55561; A61K 2039/545; A61K 2039/57; C12N 15/1117; A61P 25/28
See application file for complete search history.

(56) References Cited

U.S. PATENT DOCUMENTS

| | | |
|---|---|---|
| 6,194,388 B1 | 2/2001 | Krieg et al. |
| 6,339,068 B1 | 1/2002 | Krieg et al. |
| 6,544,518 B1 | 4/2003 | Friede et al. |
| 9,370,531 B2 | 6/2016 | Henco et al. |
| 10,383,887 B2 | 8/2019 | Wisniewski et al. |
| 10,874,725 B2 | 12/2020 | Henco et al. |
| 2004/0198680 A1 | 10/2004 | Krieg |
| 2006/0040887 A1 | 2/2006 | Karaolis |
| 2006/0159693 A1 | 7/2006 | Ward |
| 2006/0229233 A1 | 10/2006 | Frenkel et al. |
| 2006/0280733 A1 | 12/2006 | Kayed et al. |
| 2007/0142315 A1 | 6/2007 | Forsbach et al. |
| 2007/0224210 A1 | 9/2007 | Krieg et al. |
| 2008/0009455 A9 | 1/2008 | Krieg et al. |
| 2009/0082295 A1 | 3/2009 | Jungnelius et al. |
| 2010/0297108 A1 | 2/2010 | Henco et al. |
| 2010/0272785 A1 | 10/2010 | Jurk et al. |
| 2018/0110845 A1 | 4/2018 | Henco et al. |

FOREIGN PATENT DOCUMENTS

| | | |
|---|---|---|
| DE | 102005020798 A1 | 11/2006 |
| WO | WO 2000/062800 A2 | 10/2000 |
| WO | WO 01/53457 A2 | 7/2001 |
| WO | WO 2003/054161 | 7/2003 |
| WO | WO 2004/0007743 A2 | 1/2004 |
| WO | WO 2006/134423 A2 | 12/2006 |
| WO | WO 2006134423 A2 | 12/2006 |
| WO | WO 2007/030580 A2 | 3/2007 |
| WO | WO 2009/027105 A2 | 3/2009 |
| WO | 2009/105641 A2 | 8/2009 |

OTHER PUBLICATIONS

International Search Report for International Patent Application No. PCT/US2009/034677 (dated Sep. 17, 2009).
Iribarren et al., "CpG-containing oligodeoxynucleotide promotes microgliai cell uptake of amyloid beta 1-42 peptide by up-regulating the expression of the G-protein-coupled receptor mFPR2," Faseb Journal 19(14):2032-34 (2005).
Lotz et al. "Amyloid Beta Peptide 1-40 Enhances the Action of Toll-Like Receptor-2 and -4 Agonists but Antagonizes Toll-Like Receptor-9-Induced Inflammation in Primary Mouse Microglial Cell Cultures," Journal of Neurochemistry 94(2):289-98 (2005).
McCluskie et al. "Enhancement of Infectious Disease Vaccines Through TLR9-Dependent Recognition of CpG DNA," Current Topics in Microbiology and Immunology 311:155-78 (2006) (abstract).

(Continued)

*Primary Examiner* — Kimberly Ballard
(74) *Attorney, Agent, or Firm* — Troutman Pepper Hamilton Sanders LLP (Rochester)

(57) ABSTRACT

The present invention is directed to a method of preventing or reducing amyloid deposition in a subject. This method involves selecting a subject with amyloid deposits and stimulating the innate immune system of the selected subject under conditions effective to reduce the amyloid deposits. Also disclosed is a method of preventing or treating cerebral amyloidosis and Alzheimer's Disease in a subject by administering to the selected subject an agent that stimulates the innate immune system. In addition, a composition useful for the stimulation of the innate immune system of a subject exhibiting symptoms associated with amyloid deposition is disclosed.

18 Claims, 11 Drawing Sheets

Specification includes a Sequence Listing.

(56) References Cited

OTHER PUBLICATIONS

Sethi et al. "Postexposure Prophylaxis Against Prion Disease with a Stimulator of Innate Immunity," The Lancet 360(9328):229-30 (2002) (abstract).
Spinner et al., "CpG oligodeoxynucleotide-enhanced humoral immune response and production of antibodies to prion protein PrPsc in mice immunized with 139A scrapie-associated fibrils," Journal of Leukocyte Biology 81:1374-1385(2007).
Tahara et al. "Role of Toll-like Receptor Signaling in Amyloid Beta-protein Uptake and Clearance," Brain 129:3006-3019 (2006).
Crack et al. "Toll-like Receptors in the Brain and Their Potential Roles in Neuropathology," Immunology and Cell Biology 85:476-480 (2007).
Kreig, Arthur M. "Therapeutic Potential of Toll-like Receptor 9 Activation," Nature Reviews 5:471-484 (2006).
Agrawal et al. "Synthetic Agonists of Toll-like Receptors 7, 8 and 9," Biochemical Society Transactions 35(6):1461-1467 (2007).
Sugiyama et al. "CpG RNA: Identification of Novel Single-Stranded RNA That Stimulates Human CD14+CD11c+ Monocytes," The Journal of Immunology 174:2273-2279 (2005).
Written Opinion of the International Searching Authority for International Patent Application No. PCT/US2009/034677 (dated Sep. 17, 2007).
Scholtzova, H. et al., "Stimulation of innate immunity with the TLR9 Agonist CpG is beneficial in AD model mice," Abstract of presentation given at Neuroscience Aug. 17, 2007, San Diego, CA.
Wang et al., "Site-specific UBITh® amyloid-β vaccine for immunotherapy of Alzheimer's disease," Vaccine 25:3041-3052 (2007).
Lan Tao et al., "Stabilized immune modulatory RNA compounds as agonists of Toll-like Receptors 7 and 8," Proceedings of the National Academy of Sciences of the United States of America 104:13750-13755 (2007).
Vasilakos, et al., "Adjuvant Activities of Immune Response Modifier R-848: Comparison with CpG ODN," Cellular Immunology 204:64-74 (2000).
Armstrong et al., "What Determines the Molecular Composition of Abnormal Protein Aggregates in Neurodegenerative Disease?" Neuropathol. 28:351-365 (2008).
Klinman DM., "Immunotherapeutic Uses of CpG Oligodeoxynucleotides," Nat. Rev. Immunol. 4:1-10 (2004).
Written Opinion for PCT/EP2008/007127 dated Mar. 4, 2009.
International Preliminary Report on Patentability for International Application No. PCT/EP2008/007127 (dated Mar. 2, 2010).
International Search Report for International Application No. PCT/EP2008/007127 (dated Mar. 4, 2009).
Heikenwalder et al., "Lymphoid Follicle Destruction and Immunosuppression After Repeated CpG Oligodeoxynucleotide Administration," Nat. Med. 10:187-192 (2004).
Fiala et al., "Ineffective Phagocytosis of Amyloid-beta by Macrophages of Alzheimer's Disease Patients," J. Alzheimers Dis. 7:221-232 (2005).
Qiao et al., "Neuroinflammation-Induced Acceleration of Amyloid Deposition in the APPV717F Transgenic Mouse," Eur. J. Neurosci. 14:474-482 (2001).
Sheng et al., "Lipopolysaccharide-Induced-Neuroinflammation Increases Intracellular Accumulation of Amyloid Precursor Protein and Amyloid β Peptide in APPswe Transgenic Mice," Neurobiol. Disease 14:133-145 (2003).
Lee et al., "LPS-Induced Inflammation Exacerbates Phospho Tau Pathology in rTg4510 Mice," J. Neuroinflammation 7:56 (2010).
Bhaskar et al., "Regulation of Tau Pathology by the Microglial Fractalkine Receptor," Neuron 68(1): 19-31 (2010).
Tauber et al., "Stimulation of Toll-like Receptor 9 by Chronic Intraventricular Unmethylated Cytosine-Guanine DNA Infusion Causes Neuroinflammation and Impaired Spatial Memory," J. Neuropathol. Exp. Neurol. 68:1116 (2009).
Capolunghi et al., "Pharmacological Inhibition of TLR9 Activation Blocks Autoantibody Production in Human B cells from SLE Patients," Rheumatology 49(12):2281-9 (2010).
Guerrier et al., "TLR9 Drives the Development of Transitional B Cells Towards the Marginal Zone Pathway and Promotes Autoimmunity," J Autoimmun 39(3):173-9 (2012).
Azulay-Debby et al., "CpG DNA Stimulates Autoreactive Immature B cells in the Bone Marrow," Eur J Immunol. 37(6):1463-75 (2007).
Pfeifer et al., "Cerebral Hemorrhage After Passive anti-Aβ Immunotherapy," Science 298:1379 (2002).
Wilcock et al, "Passive Immunotherapy Against Abeta in Aged APP-Transgenic Mice Reverses Cognitive Deficits and Depletes Parenchymal Amyloid Deposits in Spite of Increased Vascular Amyloid and Microhemorrhage," J Neuroinflammation 1:24 (2004).
Racke et al., "Exacerbation of Cerebral Amyloid Angiopathy-Associated Microhemorrhage in Amyloid Precursor Protein Transgenic Mice by Immunotherapy is Dependent on Antibody Recognition of Deposited Forms of Amyloid beta," J Neurosci 25:629-36 (2005).
Wilcock et al., "Amyloid-beta Vaccination, but not Nitro-Nonsteriodal Anti-Inflammatory Drug Treatment, Increases Vascular Amyloid and Microhemorrhage while both Reduce Parenchymal Amyloid," Neuroscience 144:950-960 (2007).
Nelson et al., "Correlation of Alzheimer's Disease Neuropathologic Changes and Cognitive Status: a Review of the Literature," Journal of Neuropathology and Experimental Neurology 71(5):362-381 (2012).
Will R., "Acquired Prion Disease: Iatrogenic CJD, Variant CJD, Kuru," British Medical Bulletin 66:255-65 (2003).
Lee et al., "Abeta42 Immunization in Alzheimer's Disease Generates Abeta N-terminal Antibodies," Ann. Neurol. 58(3): 430-435 (2005).
Perez et al., "The Beta-amyloid Precursor Protein of Alzheimer's Disease Enhances Neuron Viability and Modulates Neuronal Polarity," J. Neurosci. 17:9407-9414 (1997).
Plant et al., "The Production of Amyloid Beta Peptide is a Critical Requirement for the Viability of Central Neurons," J. Neurosci. 23:5531-5535 (2003).
Small DH, "The Role of the Amyloid Protein Precursor (APP) in Alzheimer's Disease: Does the Normal Function of APP Explain the Topography of Neurodegeneration?," Neurochem. Res. 23(5):795-806 (1998).
Vickers JC, "A Vaccine Against Alzheimer's Disease: Developments to Date," Drugs Aging 19(7):487-494 (2002).
Hampel et al., "The Future of Alzheimer's Disease: The Next 10 years," Progress Neurobiol. 95:718-728 (2011).
Lemere et al., "Amyloid-beta Immunotherapy for the Prevention and Treatment of Alzheimer's Disease: Lessons From Mice, Monkeys, and Humans," Rejuvenation Res. 9(1):77-84 (2006).
Liu et al., "Amyloid-beta Peptide Alters Intracellular Vesicle Trafficking and Cholesterol Homeostasis," Proc Natl Acad Sci USA 95:13266-13271 (1998).
Masliah et al., "Amyloid Protein Precursor Stimulates Excitatory Amino Acid Transport," J. Biol. Chem. 273(20):12548-12554 (1998).
Examination Report for EP08785778.5 dated Jul. 22, 2016.
Cunningham et al., "Systemic Inflammation Induces Acute Behavioral and Cognitive Changes and Accelerates Neurodegenerative Disease," Biol. Psychiatry 65(4):304-12 (2009).
Cunningham et al., "Central and Systemic Endotoxin Challenges Exacerbate the Local Inflammatory Response and Increase Neuronal Death During Chronic Neurodegeneration," J. Neurosci. 25(40):9275-84 (2005).
Perry, "The Influence of Systemic Inflammation on Inflammation in the Brain: Implications for Chronic Neurodegenerative Disease," Brain Behav. Immun. 18(5):407-13 (2004).
Combrinck et al., "Peripheral Infection Evokes Exaggerated Sickness Behaviour in Pre-Clinical Murine Prion Disease," Neurosci. 112(1):7-11 (2002).
Sparwasser et al., "Bacterial CpG-DNA Activates Dendritic Cells in Vivo: T Helper Cell-Independent Cytotoxic T Cell Responses to Soluble Proteins," Eur. J. Immunol. 30:3591-7 (2000).
Zimmermann et al., "Cutting Edge: CpG Oligodeoxynucleotides Trigger Protective and Curative Th1 Responses in Lethal Murine Leishmaniasis," J. Immunol. 160:3627-30 (1998).
Rogers et al., "Metal and Inflammatory Targets for Alzheimer's Disease," Curr. Drug Targets 5(6):535-51 (2004).

(56) References Cited

OTHER PUBLICATIONS

Lahiri, "Molecular Analysis of the Promoter Region of the Gene Encoding the Beta-Amyloid Precursor Protein," Indian J. Biochem. Biophys. 32(6):329-35 (1995).
Yang et al., "Upregulation of Amyloid Precursor Protein Gene Promoter in Rat Primary Hippocampal Neurons by Phorbol Ester, IL-1 and Retinoic Acid, but not by Reactive Oxygen Species," Brain Res. Mol. Brain Res. 18(60):40-9 (1998).
Ge et al., "Regulation of Promoter Activity of the APP gene by Cytokines and Growth Factors: Implications in Alzheimer's Disease," Ann N Y Acad. Sci. 973:463-7 (2002).
Kitazawa et al., "Lipopolysaccharide-Induced Inflammation Exacerbates Tau Pathology by a Cyclin-Dependent Kinase 5-Mediated Pathway in a Transgenic Model of Alzheimer's Disease," J. Neurosci. 25(39):8843-53 (2005).
Schneider et al., "Hyperphosphorylation and Aggregation of Tau in Experimental Autoimmune Encephalomyelitis," J. Biol. Chem. 279(53):55833-9 (2004).
Ghosh et al., "Sustained Interleukin-1β Overexpression Exacerbates Tau Pathology Despite Reduced Amyloid Burden in an Alzheimer's Mouse Model," J. Neurosci. 33(11):5053-64 (2013).
Aguzzi et al., "Antiprion Immunotherapy: To Suppress or to Stimulate?," Nat. Rev. Immunol. 4:725-736 (2004).
Bremer et al., "Repetitive Immunization Enhances the Susceptibility of Mice to Peripherally Administered Prions," PLoS ONE 4(9):e7160 (2009).
Guillot-Sestier et al., "Innate Immunity in Alzheimer's Disease: A Complex Affair," CNS Nerol. Disord. Drug Targets 12(5):593-607 (2013).
Scholtzova et al., "Innate Immune Stimulation via Toll-Like Receptor 9 Ameliorates Vascular Amyloid Pathobiology in Tg-SwDI Mice with Associated Cognitive Benefits," J. Neurosci 37(4):936-959 (2017).
Selles et al., "Immunomodulation via Toll-Like Receptor 9: An Adjunct Therapy Strategy against Alzheimer's Disease?" J. Neurosci. 37(4):4864-4867 (2017).
Scholtzova et al., "Amyloid β and Tau Alzheimer's Disease Related Pathology is Reduced by Toll-like Receptor 9 Stimulation," Acta Neuropathol Commun. 2:101 (2014).
Alzoforum, "Inflammation Helps Microglia Clear Amyloid from AD Brains," (retrieved on Jul. 27, 2017 from www.alzoforum.org/news/conference-coverage/inflammation-helps-microglia-clear-a . . .).
Restriction Requirement in U.S. Appl. No. 15/177,980 dated Mar. 9, 2017.
Office Action in U.S. Appl. No. 15/177,980 dated Jun. 16, 2017.
Restriction Requirement in U.S. Appl. No. 15/845,110 dated Oct. 4, 2018.
Communication for EP08785778.5 dated Jan. 11, 2018.
Intention to Grant for EP08785778.5 dated Aug. 16, 2018.
Examination Report for European Patent Application No. 08785778.5 (dated Jun. 11, 2014) which is a national stage application for PCT/EP2008/007127.
Scholtzova, H. et al., "Induction of Toll-Like Receptor 9 Signaling as a Method for Ameliorating Alzheimer's Disease-Related Pathology," J. Neuro. 29(6):1846-54 (2009).
Vollmer et al., "Immunotherapeutic Applications of CpG Oligonucleotide TLR9 Agonists," Adv Drug Deliv Rev. 61(3):195-204 (2009).
Hartman et al., "Delineation of a CpG Phosphorothioate Oligodeoxynucleotide for Activating Primate Immune Responses In Vitro and In Vivo," J. Immunol. 164(3): 1617-24 (2000).
Scheiermann et al., "Clinical Evaluation of CpG Oligonucleotides as Adjuvants for Vaccines Targeting Infectious Diseases and Cancer," Vaccine 32: 6377-6389 (2014).
Amendment for U.S. Appl. No. 12/733,437 dated Jan. 4, 2016.
Mutwiri et al., "Biological Activity of Immunostimulatory CpG DNA Motifs in Domestic Animals," Veterinary Immunology and Immunopathology 91:89-103 (2003).
Office Action in U.S. Appl. No. 15/845,110 dated Apr. 19, 2019.
Office Action in U.S. Appl. No. 15/845,110 dated Jan. 23, 2020.
Klinman DM et al. Repeated administration of synthetic oligodeoxynucleotides expressing CpG motifs provides long-term protection against bacterial infection. Infection & Immunity, 67(11), 5658-5663. (Year: 1999).
Definition for "subclinical", retrieved from Wiktionary (en.wiktionary.org/w/index.php?title=subclinical&oldid=51386311) on Jan. 16, 2020. (Year 2020).
Restriction Requirement in U.S. Appl. No. 12/918,739 dated Aug. 9, 2012.
Office Action in U.S. Appl. No. 12/918,739 dated Oct. 10, 2012.
Office Action in U.S. Appl. No. 12/918,739 dated Apr. 23, 2013.
Office Action in U.S. Appl. No. 12/918,739 dated Nov. 21, 2013.
Office Action in U.S. Appl. No. 12/918,739 dated Jan. 27, 2015.
Office Action in U.S. Appl. No. 12/918,739 dated Aug. 13, 2015.
Office Action in U.S. Appl. No. 12/918,739 dated Sep. 2, 2016.
Office Action in U.S. Appl. No. 12/918,739 dated Mar. 20, 2017.
Office Action in U.S. Appl. No. 12/918,739 dated Dec. 28, 2017.
Restriction Requirement for U.S. Appl. No. 15/845,110 dated Oct. 4, 2018.
Baines & Celis," Immune-Mediated Tumor Regression Induced by CpG-Containing Oligodeoxynucleotides," Clin. Cancer Res. 9:2693-2700 (2003).
Kielian T., "Toll-Like Receptors in Central Nervous System Glial Inflammation and Homeostasis," J. Neurosci. Res. 83 (5):711-730 (2006).
Shen et al, "CpG Oligodeoxynucleotides Prevent the Development of Scleroderma-Like Syndrome in Tight-Skin Mice by Stimulating a Th1 Immune Response," J. Invest. Dermatol. 124, 1141-1148 (2005).
Von Beust et al., "Improving the Therapeutic Index of CpG Oligodeoxynucleotides by Intralymphatic Administration," Eur. J. Immunol. 35:1869-1876 (2005).
Written Opinion for PCT/EP2008/007127 (dated Feb. 28, 2010).

Figures 1A-D

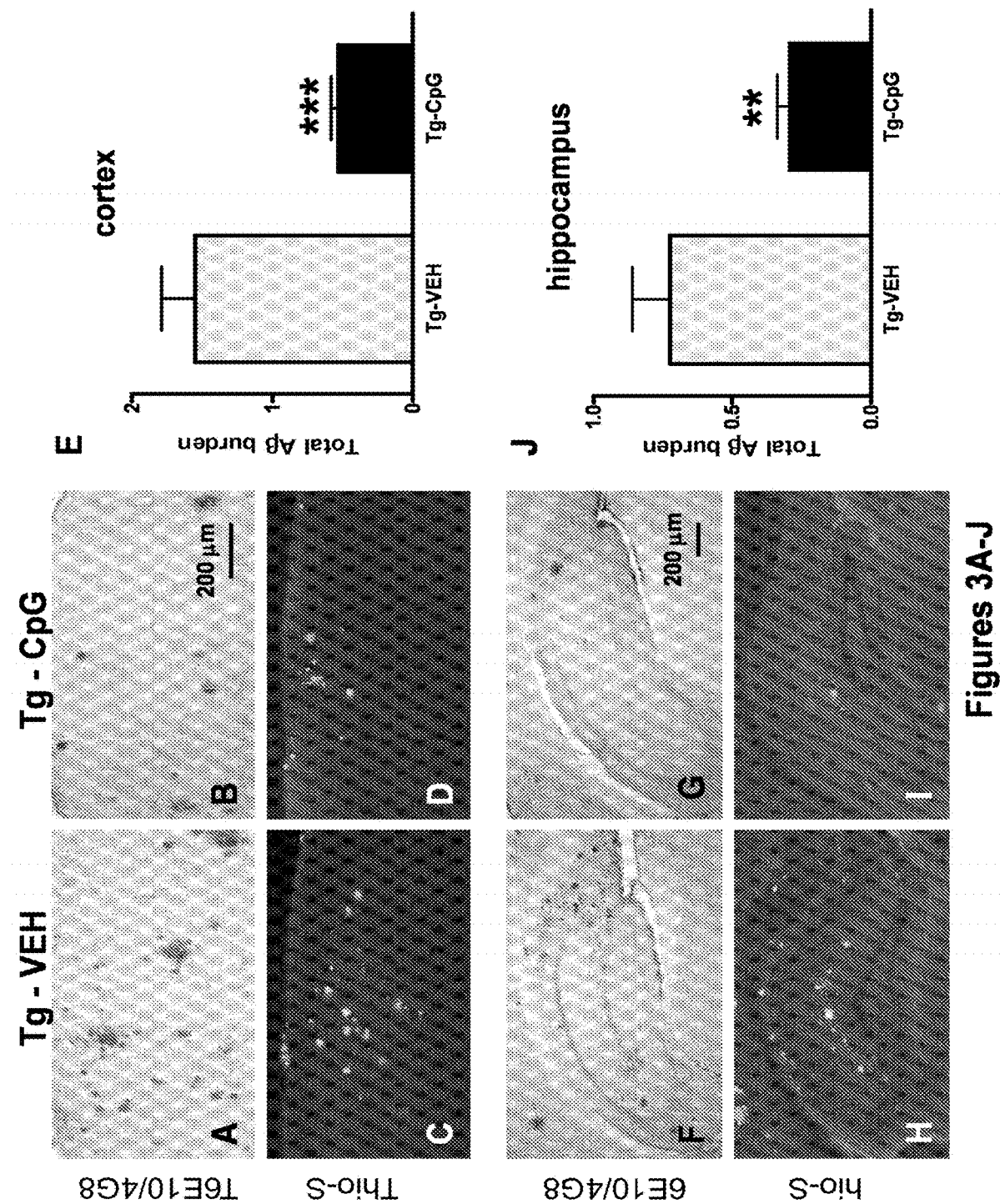
Figures 3A-J

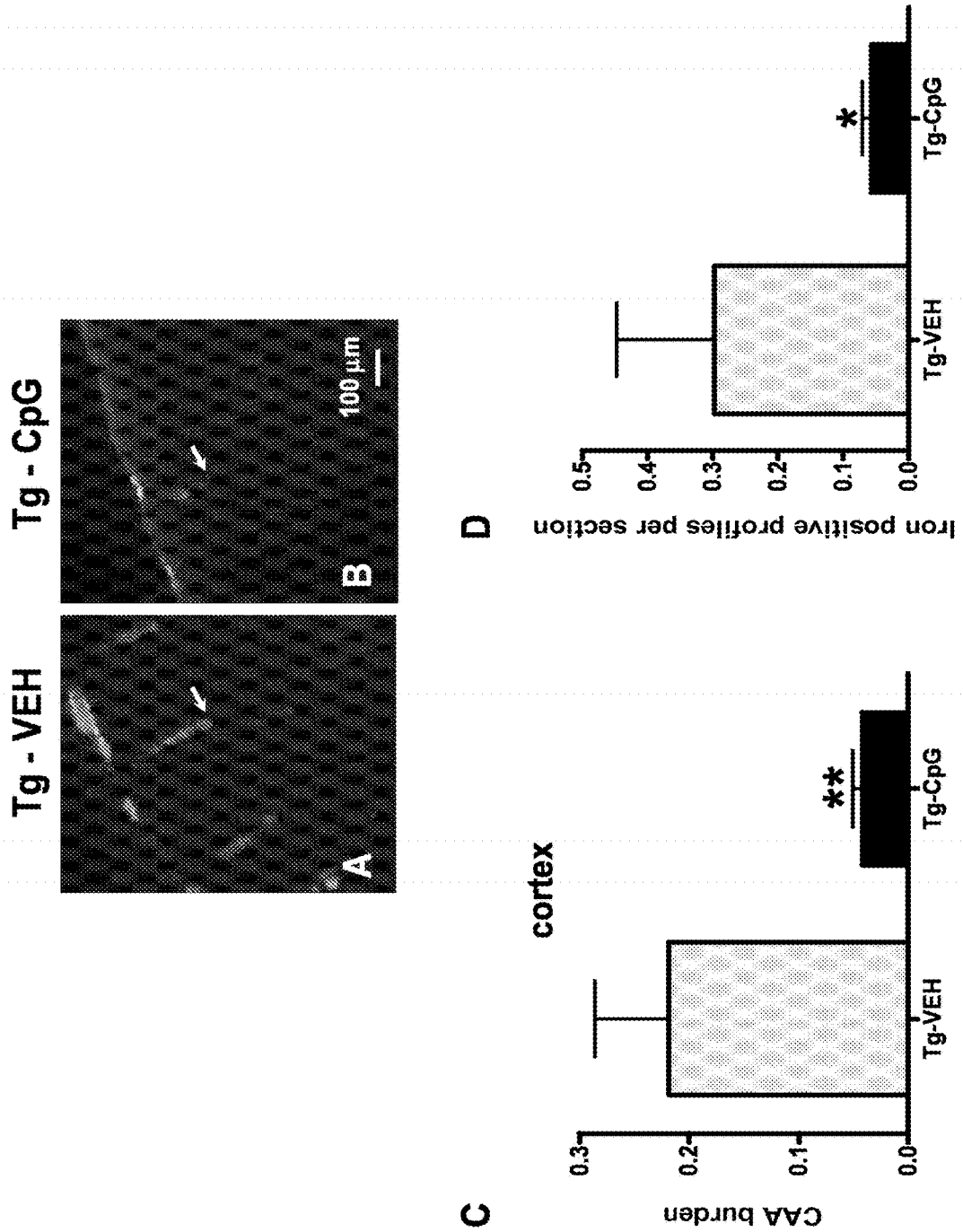
Figures 4A-D

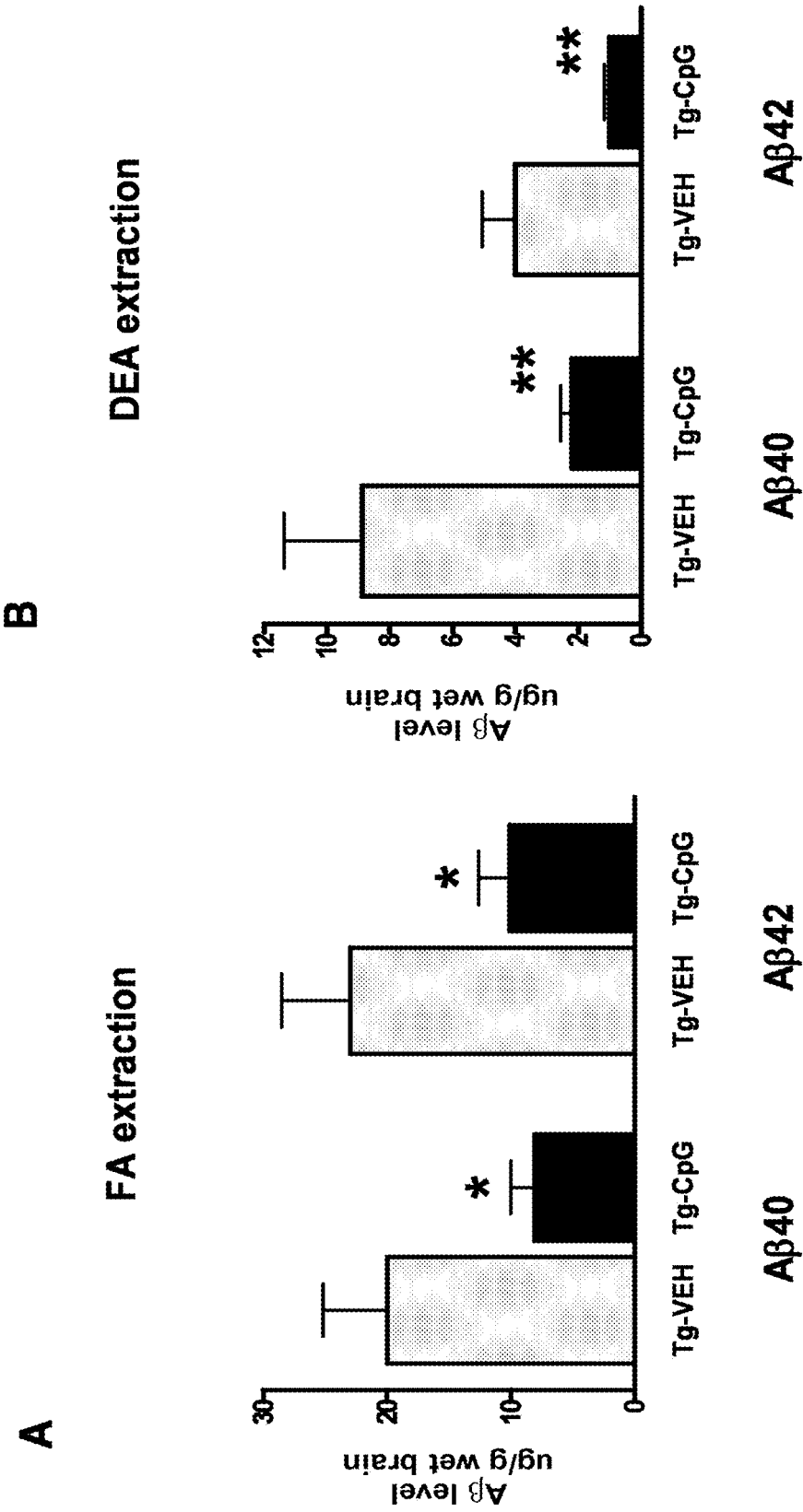
Figures 5A-B

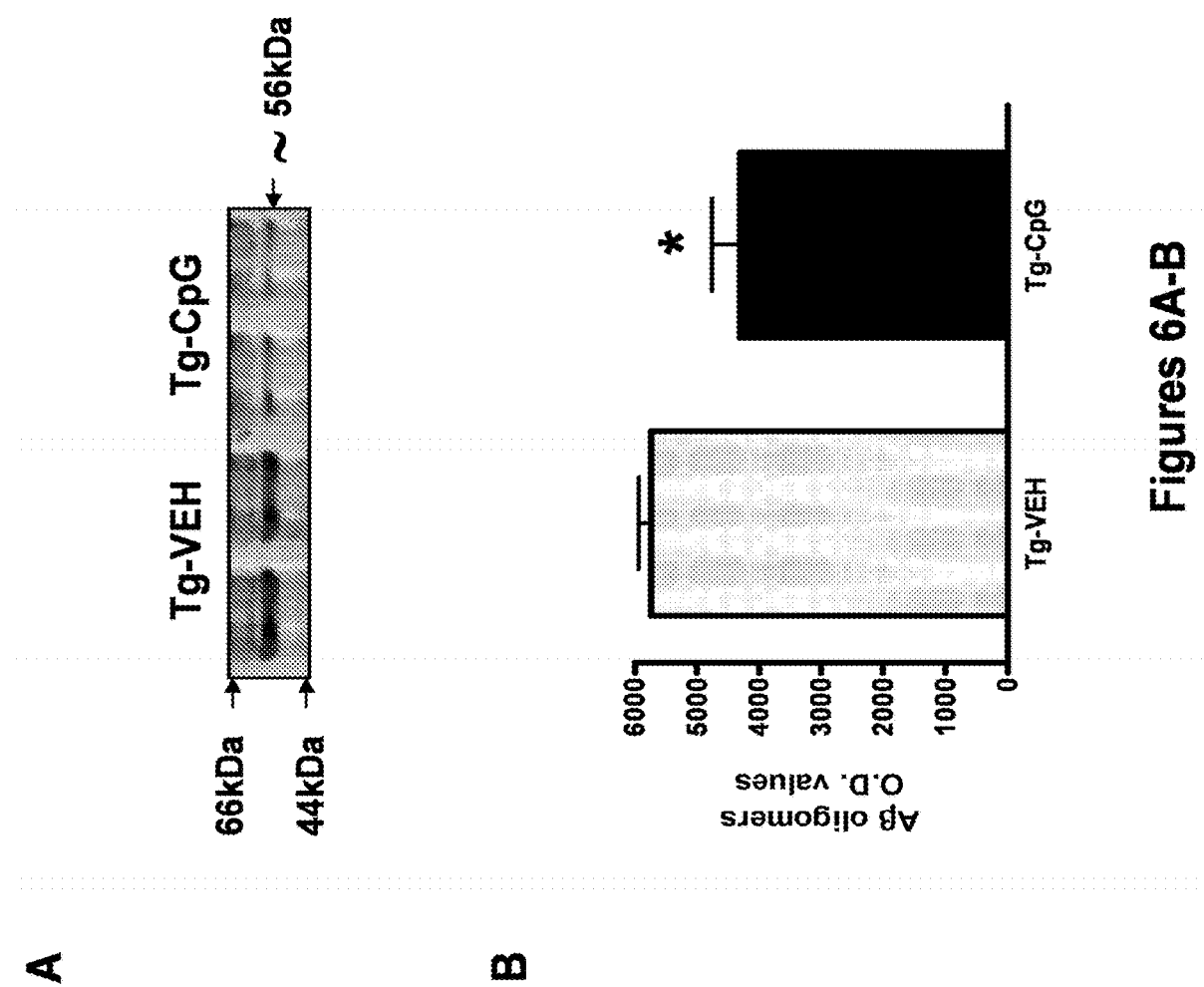
Figures 6A-B

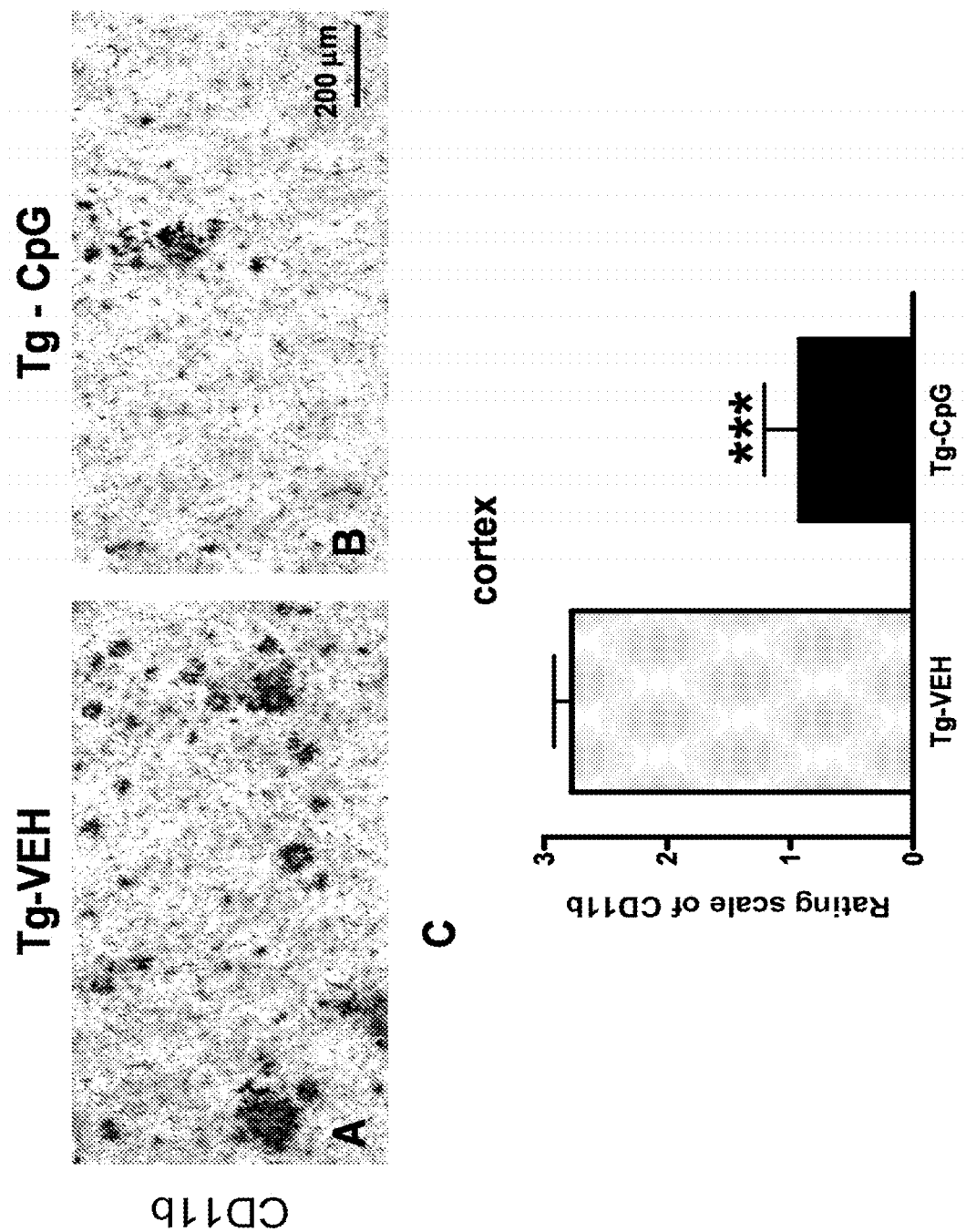
Figures 7A-C

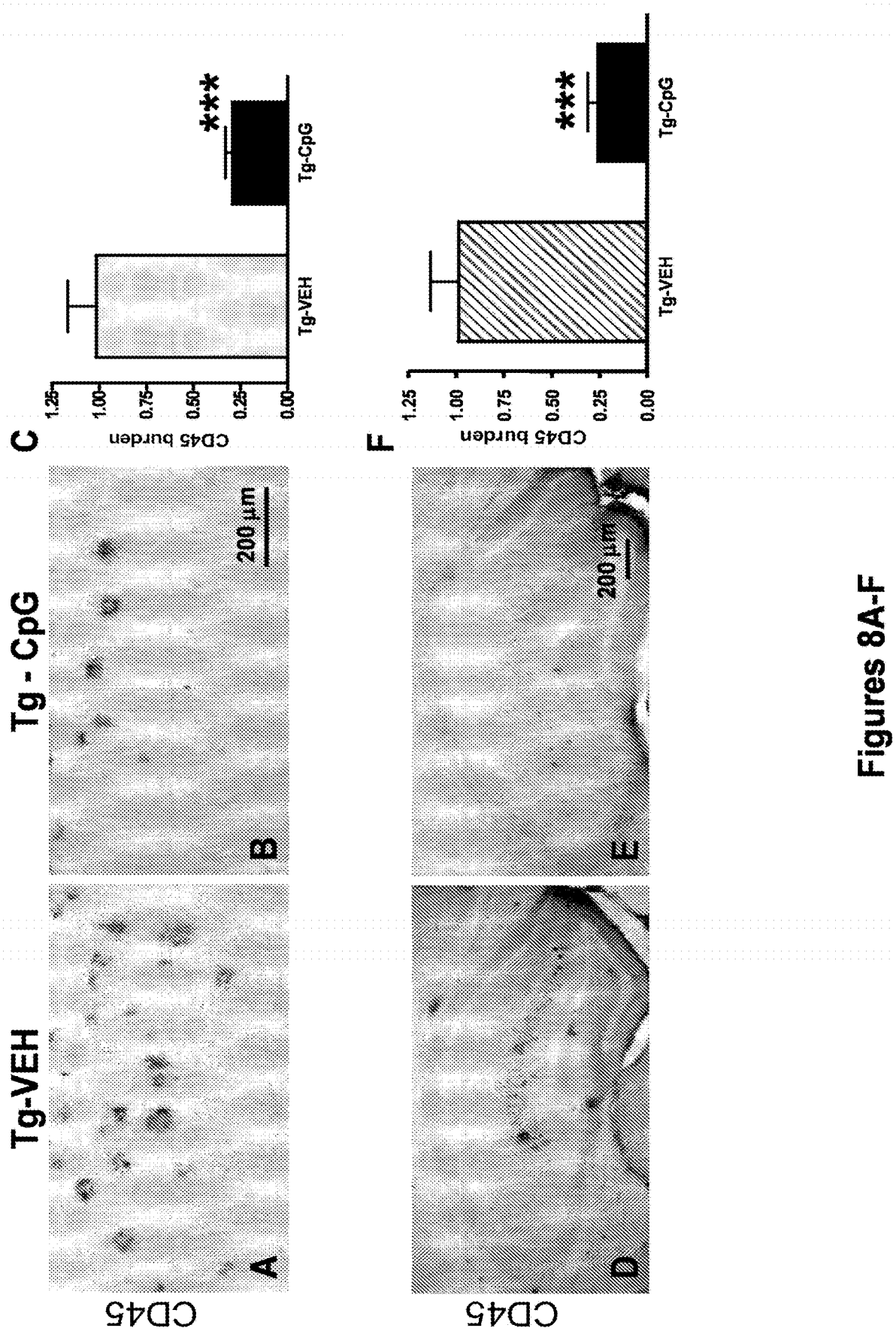
Figures 8A-F

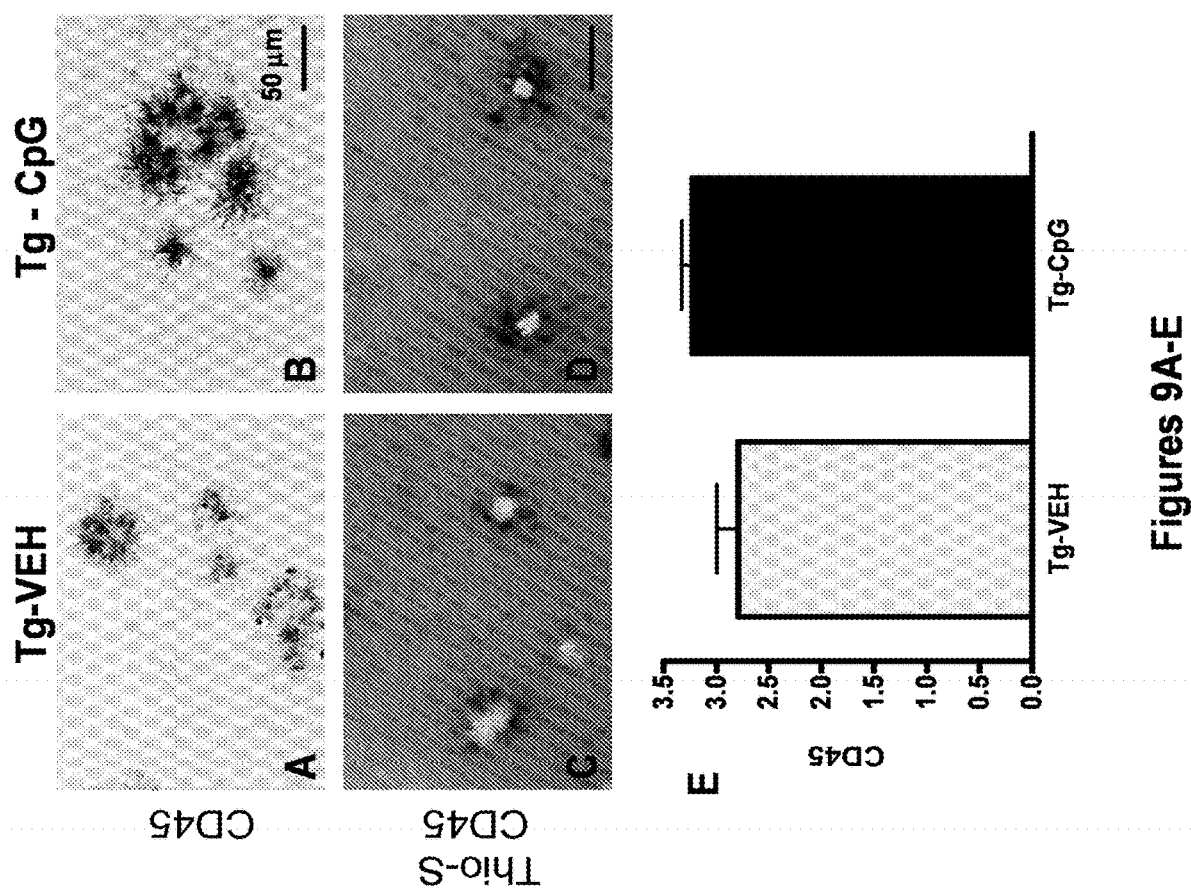
Figures 9A-E

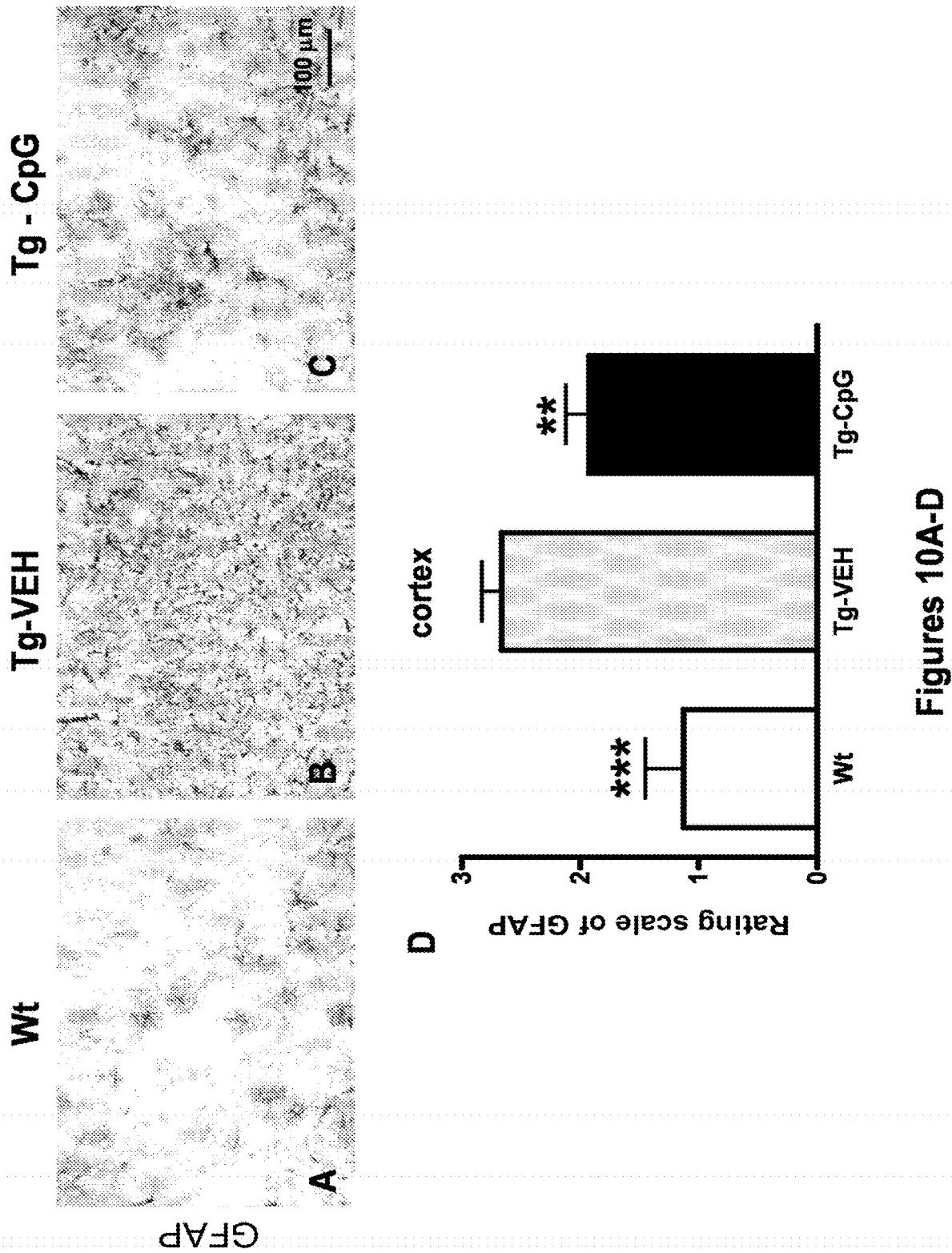
Figures 10A-D

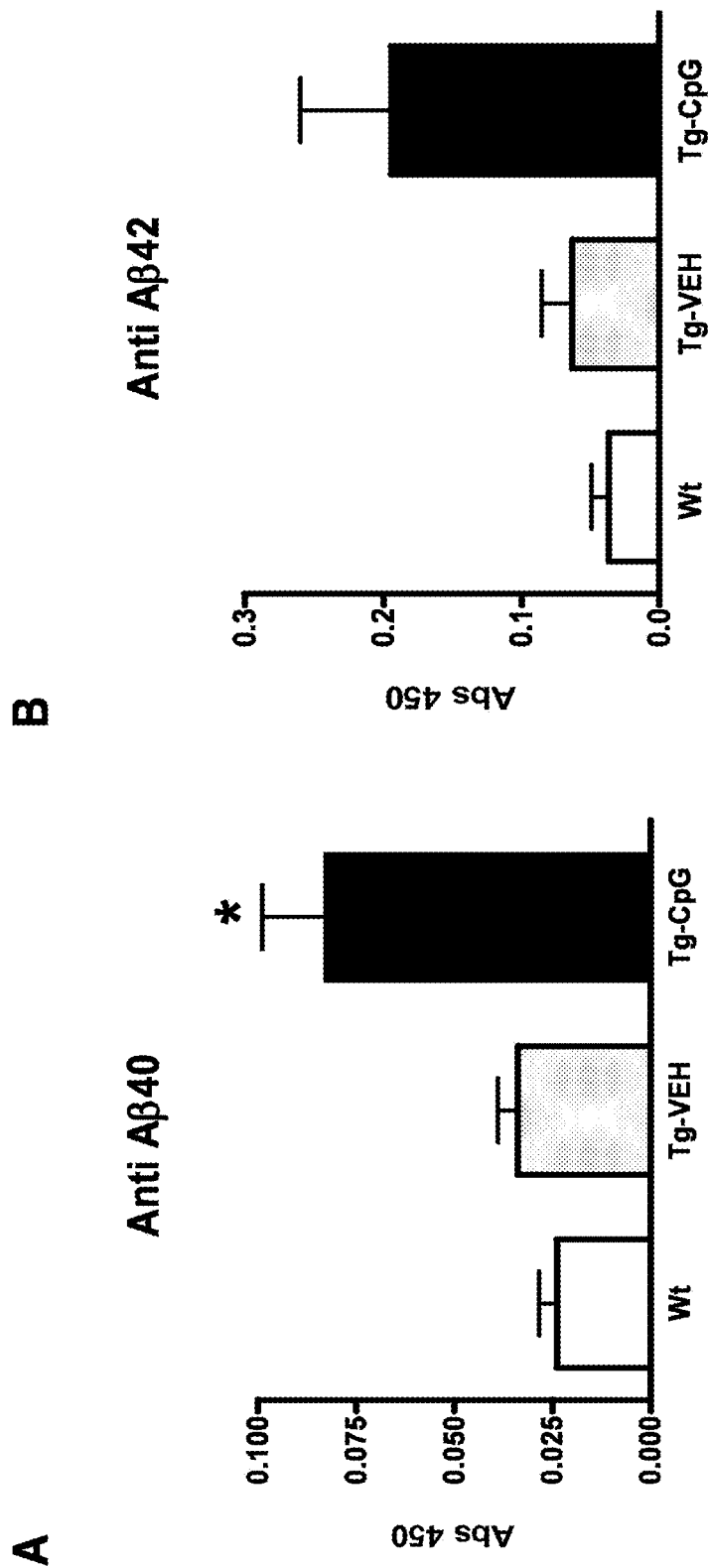
Figures 11A-B

PREVENTING AND TREATING AMYLOID-BETA DEPOSITION BY STIMULATION OF INNATE IMMUNITY

This application is a continuation of U.S. patent application Ser. No. 12/918,739, filed Sep. 21, 2010, which is a national stage application under 35 U.S.C. § 371 of PCT/US2009/034677, filed Feb. 20, 2009, which claims the priority benefit of U.S. Provisional Patent Application Ser. No. 61/030,089, filed Feb. 20, 2008, which are hereby incorporated by reference in their entirety.

This invention was made with government support under Grant No. AG20245 awarded by National Institutes of Health. The government has certain rights in the invention.

FIELD OF THE INVENTION

The present invention relates to preventing and treating Amyloid-β deposition by stimulation of innate immunity.

BACKGROUND OF THE INVENTION

Alzheimer's disease (AD) is a degenerative brain disorder characterized clinically by progressive loss of memory, cognition, reasoning, judgment and emotional stability that gradually leads to profound mental deterioration and ultimately death. AD is a very common cause of progressive mental failure (dementia) in aged humans and is believed to represent the fourth most common medical cause of death in the United States. AD begins slowly, first affecting the parts of the brain controlling thought, memory, and language. As symptoms worsen, patients may not remember family members, or have trouble speaking, reading, or writing. In later disease progression, AD patients may become anxious, aggressive, or wander away from home. Eventually needing total care, the AD patient may cause great stress for family members who care for them.

AD has been observed in all races and ethnic groups worldwide and presents a major present and future public health problem. As many as 4.5 million Americans suffer from AD. The disease usually begins after age sixty, and risk goes up with age. While younger people also may get AD, it is much less common. About five percent of men and women ages sixty-five to seventy-four have AD, and nearly half of those age eighty-five and older may have the disease. It is important to note, however, that AD is not a normal part of aging. AD is at present incurable. No treatment that effectively prevents AD or reverses its symptoms or course is currently known.

The deposition of amyloid-β (Aβ) peptides in the central nervous system in the form of amyloid plaques is one of the hallmarks of AD (U.S. Patent Publication No. 20040214774 to Wisniewski et al.; U.S. Pat. No. 6,114,133 to Seubert; Wegiel et al., "Alzheimer Dementia Neuropathology," in *Dementia: Presentations, Differential Diagnosis & Nosology*, 89-120 (Emery & Oxman, eds., 2003). Several lines of evidence favor the conclusion that Aβ accumulation destroys neurons in the brain, leading to deficits in cognitive abilities. Because accumulation of Aβ appears to be the result of a shift in equilibrium from clearance toward deposition, identifying and promoting mechanisms that enhance Aβ clearance from the brain is highly desirable.

Vaccination was the first treatment approach which has been shown to have genuine impact on disease process, at least in animal models of AD (Sadowski et al., "Disease Modifying Approaches for Alzheimer's Pathology," *Current Pharmaceutic Design*, 13:1943-54 (2007); Wisniewski et al., "Therapeutic Approaches for Prion and Alzheimer's Diseases," *FEBS J*. 274:3784-98 (2007); Wisniewski et al., "Immunological and Anti-Chaperone Therapeutic Approaches for Alzheimer Disease," *Brain Pathol*. 15:72-77 (2005)). Vaccination of AD transgenic (Tg) mice with Aβ1-42 or Aβ homologous peptides co-injected with Freund's adjuvant prevented the formation of Aβ deposition and as a consequence eliminate the behavioral impairments that are related to Aβ deposition (Schenk et al., "Immunization with Amyloid-Beta Attenuates Alzheimer-Disease-Like Pathology in the PDAPP Mouse," *Nature* 400:173-77 (1999); Sigurdsson et al., "Immunization with a Nontoxic/Nonfibrillar Amyloid-beta Homologous Peptide Reduces Alzheimer's Disease-Associated Pathology in Transgenic Mice," *Am. J. Pathol*. 159:439-47 (2001); Morgan et al., "A Beta Peptide Vaccination Prevents Memory Loss in an Animal Model of Alzheimer's Disease," *Nature* 408:982-85 (2001); Janus et al., "A Beta Peptide Immunization Reduces behavioural Impairment and Plaques in a Model of Alzheimer's Disease," *Nature* 408:979-82 (2000)).

The striking biological effect of the vaccine in preclinical testing and the apparent lack of side effects in AD Tg mice encouraged Elan Pharmaceuticals, Inc./Wyeth Research to launch clinical trials with a vaccine designated as AN1792 which contained pre-aggregated Aβ1-42 and QS21 as an adjuvant. It was thought that this type of vaccine design would induce a strong adaptive cell mediated immune response, because QS21 is known to be a strong inducer of T-helper type-1 (Th-1) lymphocytes. The phase II of the trial was prematurely terminated when 6% of vaccinated patients manifested symptoms of acute meningoencephalitis. An autopsy performed on one of the affected patients revealed an extensive cytotoxic T-cell reaction surrounding some cerebral blood vessels. Analysis of the Aβ load in the brain cortex, however, suggested that Aβ clearance had occurred (Nicoll et al., "Neuropathology of Human Alzheimer Disease after Immunization with Amyloid-beta Peptide: A Case Report," *Nature Med*. 9:448-52 (2003)). Neuropsychiatric testing of vaccinated patients who mounted an immune response showed a modest but statistically significant cognitive benefit, demonstrating an improvement on some cognitive testing scales comparing to baseline and a slowed rate of disease progression in patients who had developed antibodies to Aβ (Hock et al., "Antibodies Against Beta-Amyloid Slow Cognitive Decline in Alzheimer's Disease," *Neuron* 38:547-54 (2003)). This indicated that the vaccination approach could be beneficial for human AD patients, but that the concept of the vaccine may need redesigning.

Given the significant impact of AD, there is a great need to discover, develop, and test new treatments that may be helpful in preventing and/or treating this devastating disease. The present invention is directed to achieve these objectives.

SUMMARY OF THE INVENTION

The present invention is directed to a method of preventing and reducing amyloid deposition in a subject. This method involves selecting a subject with amyloid deposits and stimulating the innate immune system of the selected subject under conditions effective to reduce the amyloid deposits.

Another aspect of the present invention is directed to a method of preventing or treating cerebral amyloidosis in a subject. This method comprises selecting a subject susceptible to or afflicted with cerebral amyloidosis and administering to the selected subject an agent that stimulates the innate immune system of the subject under conditions effective to prevent or treat cerebral amyloidosis.

Another aspect of the present invention is directed to a method of preventing or treating AD in a subject. This method comprises selecting a subject susceptible to or afflicted with AD and administering to the selected subject an agent that stimulates the innate immune system of the subject under conditions effective to prevent or treat AD.

A further aspect of the present invention relates to a composition useful for the stimulation of the innate immune system of a subject exhibiting symptoms associated with amyloid deposition. This composition includes an oligonucleotide bearing at least one unmethylated CpG motif and a pharmaceutically effective carrier.

Another aspect of the present invention relates to a pharmaceutical composition for preventing or reducing amyloid deposition, preventing or treating cerebral amyloidosis, or preventing or treating Alzheimer's disease. The pharmaceutical composition contains an agent capable of stimulating the innate immune system of a subject and a pharmaceutically effective carrier.

The benefits of the present invention harness one of the most potent methods to stimulate the innate immune system: via the Toll-like receptors. The Toll-like receptors (TLRs) are a family of innate immune mediators that are expressed by a variety of immune and non-immune cells (Krieg, "CpG Motifs in Bacterial DNA and their Immune Effects," *Annu Rev Immunol* 20:709-60 (2002) which is hereby incorporated by reference in its entirety. In vertebrates, TLRs function primarily to recognize invading microbial pathogens, including bacteria, viruses, fungi, and protozoans, and activate appropriate signaling pathways to effectively clear the threat. The recognition of microbial pathogens by TLRs is mediated through the binding of pathogen-specific structures "unique" to each individual class of pathogen. There are thirteen distinct TLR family members currently known in mammals, of which the pathogen-specific structures recognized by ten (TLR1 to TLR9, and TLR11) have been identified.

BRIEF DESCRIPTION OF THE DRAWINGS

FIGS. 3A-J illustrate the decrease in cortical and hippocampal amyloid plaque burden in APP Tg2576 mice with CpG ODN treatment. Histological analysis of APP Tg mice depict the difference in Aβ burden. Aβ immunostaining (antibodies 6E10/4G8) showed greater Aβ accumulation in cortical (FIG. 3A) and hippocampal (FIG. 3F) sections of vehicle-treated mice compared to sections from CpG ODN-treated APP mice (FIGS. 3B and 3G). Similarly, Thioflavin-S cortical and hippocampal staining also revealed differences between vehicle-treated (FIGS. 3C and 3H) and CpG ODN-treated (FIGS. 3D and 3I) APP Tg2576 mice. Stereological analysis of total amyloid burden (Aβ load) showed a significant reduction in APP-Tg mice treated with CpG ODN compared to age-matched Tg control mice treated with vehicle. There was a 66% reduction in cortical (FIG. 3E) amyloid burden (*p=0.0001; two-tailed t-test) and a 59% reduction in hippocampal (FIG. 3J) amyloid burden (p=0.002) as quantified using unbiased random sampling of scheme and semi-automated image analysis system. The scale bar in FIG. 3B corresponds to cortical images A-D. The scale bar in FIG. 3G corresponds to hippocampal images F-I.

FIGS. 4A-D demonstrate analysis of Aβ burden in the vasculature (CAA burden) and brain microhemorrhages. Thioflavin-S staining (FIGS. 4A and 4B) revealed a visible reduction in the CAA burden of the penetrating cortical vessels (white arrowhead). There was an 80% decrease (FIG. 4C) in CAA burden in CpG ODN-treated Tg2576 mice (Tg-CpG vs Tg-vehicle, **p=0.0039). Quantification of CAA-associated microhemorrhages (Perl's stain) also revealed a significant reduction (FIG. 4D) of iron positive profiles per brain section in CpG-treated group (Tg-CpG vs Tg-vehicle, *p=0.029).

FIGS. 5A-B indicate that treatment with CpG ODN significantly decreased total (FIG. 5A) and soluble (FIG. 5B) brain Aβ levels in Tg2576 mice. FIG. 5A shows a 59% reduction in total Aβ (*p=0.019) and a 56% reduction in Aβ42 (*p=0.026). FIG. 5B show a 75% reduction in soluble Aβ40 (p=0.003) and a 74% reduction in soluble Aβ42 (p=0.0019).

FIGS. 6A-B show Western blot detection and densitometric analysis of A11 immunoreactive oligomer-specific bands. Western blot (FIG. 6A) of brain homogenates stained with A11 oligomer-specific polyclonal antibody and densitometric analysis (FIG. 6B) of the oligomer-specific (56 kDa) band shows significant difference between CpG ODN-treated and vehicle-treated Tg animals (*p=0.033).

FIGS. 7A-C show that CpG ODN treatment reduced overall cortical CD11b immunoreactivity in APP Tg2576 mice. Immunostaining (FIGS. 7A and 7B) with CD11b microglial marker, followed by semiquantitative analysis (FIG. 7C), revealed a significant reduction in cortical microgliosis in CpG ODN-treated (FIG. 7B) compared to vehicle-treated (FIG. 7A) Tg animals (Tg-CpG vs Tg-vehicle, ***p=0.0001). The degree of microgliosis was graded on a scale from 0 to 3.

FIGS. 8A-F show a reduction in cortical and hippocampal CD45 immunoreactivity (CD45-expressing microglial load) in CpG ODN-treated Tg2565 mice. Cortical (FIGS. 8A and 8B) and hippocampal (FIGS. 8D and 8E) CD45 immunohistochemistry indicated an overall reduction in microglial activity in CpG ODN-treated mice (FIGS. 8B and 8E). Quantitative stereological analysis within the cortex revealed a 71% reduction (*p=0.001) in CD45 immunoreactivity in CpG treated Tg mice compared to control Tg mice (FIG. 8C). Likewise, CD45 immunoreactivity within the hippocampus was reduced by 73% (*p=0.001) in Tg-CpG group compared to Tg-vehicle group (FIG. 8F). The scale bars in FIGS. 8B and E correspond to cortical and hippocampal images, respectively.

FIGS. 9A-E depict microglial reactivity around the plaques. Immunostaining of CD45 microglia alone (FIGS. 9A and 9B) and with Thioflavin-S (FIGS. 9C and 9D) followed by semiquantitative analysis (FIG. 9E) demonstrated an increasing trend in CD45 immunoreactivity around remaining plaques in CpG ODN-treated group (Tg-CpG vs Tg-vehicle, *p=0.047). Scale bar, 50 Gm.

FIGS. 10A-D indicate that treatment with CpG ODN reduced cortical GFAP reactive astrocytosis in APP Tg2576 mice. GFAP immunostaining in WT (FIG. 10A), Tg-vehicle treated (FIG. 10B), and Tg-CpG ODN treated (FIG. 10C) followed by semiquantitative analysis (FIG. 10D) revealed fewer activated astrocytes in CpG ODN-treated Tg animals compared to vehicle-treated animals (Tg-CpG vs Tg-vehicle, p=0.006; Tg-vehicle vs Wt, *p=0.0005; Tg-CpG vs Wt, p=0.054). Reactive astrocytosis was rated on a scale of 0.5-3.

FIGS. 11A-B are bar graphs showing autoantibody responses to Aβ40 and Aβ42. At 17 months of age, there was a significantly higher autoantibody response towards Aβ40 (FIG. 11A) and a trend for a higher response to Aβ42 (FIG. 11B) in CpG ODN-treated Tg mice when compared to vehicle-treated Tg mice. The Tg-vehicle mice did not differ from the wild-type controls. FIG. 11A: Tg-Cpg vs Tg-vehicle *p=0.017; Tg-vehicle vs Wt, p=0.24; Tg-CpG vs Wt, *p=0.042). FIG. 11B: Tg-CpG vs Tg-vehicle p=0.09; Tg-vehicle vs Wt, p=0.44; Tg-CpG vs Wt, p=0.15. No apparent differences were observed between the groups in 12-month-old animals.

DETAILED DESCRIPTION OF THE INVENTION

Figure 1:
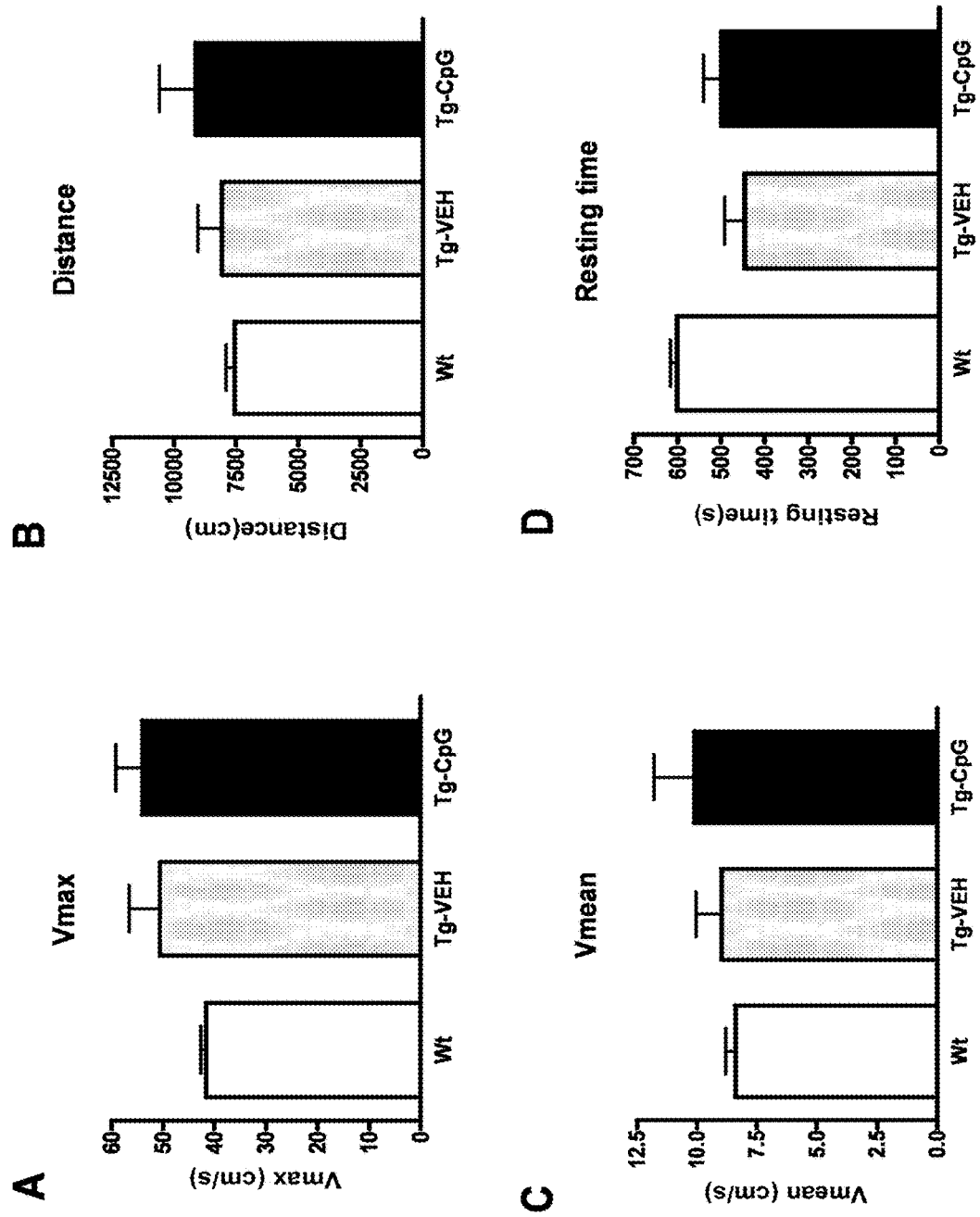
FIGS. 1A-D are bar graphs representing locomotor activity assessment in Tg2576 APP (Tg) mice treated with TLR9 agonist CpG oligodeoxynucleotide (ODN) 1826 or vehicle and their wild-type (Wt) littermate controls. At 16 months of age (post treatment), both Tg groups and their wild-type (Wt) littermates did not differ in any of the locomotor parameters measured (distance traveled (FIG. 1B), maximum speed (FIG. 1A), average speed (FIG. 1C) and resting time (FIG. 1D). Error bars are standard error of the means, which applies also to all subsequent figures. No significant differences were observed between groups.

The present invention is directed to a method of reducing amyloid deposition in a subject. This method involves selecting a subject with amyloid deposits and stimulating the innate immune system of the selected subject under conditions effective to reduce the amyloid deposits.

As used herein, "amyloid" encompasses any insoluble fibrous protein aggregate that is deposited in the body. Amyloid deposition may be organ-specific (e.g. central nervous system, pancreas, etc.) or systemic. In accordance with this aspect of the invention, amyloidogenic proteins subject to deposition include beta protein precursor, prion, α-synuclein, tau, ABri precursor protein, ADan precursor protein, amylin, apolipoprotein AI, apolipoprotein AII, lyzozyme, cystatin C, gelsolin, protein, atrial natriuretic factor, calcitonin, keratoepithelin, lactoferrin, immunoglobulin light chains, transthyretin, A amyloidosis, β2-microglobulin, immunoglobulin heavy chains, fibrinogen alpha chains, prolactin, keratin, and medin. Amyloid deposition may occur as its own entity or as a result of another illness (e.g. multiple myeloma, chronic infection, or chronic inflammatory disease). Therefore, the methods of the present invention can further be used to treat a subject having a condition or disease that is associated with, or resulting from, the deposition of amyloidogenic proteins. Such conditions include, but are not limited to, Alzheimer's disease, diffuse Lewy body disease, Down syndrome, hereditary cerebral hemorrhage with amyloidosis, Creutzfeldt-Jakob disease, Gerstmann-Straussler-Scheinker disease, fatal familial insomnia, British familial dementia, Danish familial dementia, familial corneal amyloidosis, Familial corneal dystrophies, medullary thyroid carcinoma, insulinoma, type 2 diabetes, isolated atrial amyloidosis, pituitary amyloidosis, aortic amyloidosis, plasma cell disorders, familial amyloidosis, senile cardiac amyloidosis, inflammation-associated amyloidosis, familial Mediterranean fever, dialysis-associated amyloidosis, systemic amyloidosis, and familial systemic amyloidosis.

Another aspect of the present invention is directed to a method of preventing or treating cerebral amyloidosis in a subject. This method comprises selecting a subject susceptible to or afflicted with cerebral amyloidosis and administering to the selected subject an agent that stimulates the innate immune system of the subject under conditions effective to prevent or treat cerebral amyloidosis.

As used herein, "cerebral amyloidosis" refers to a condition where an amyloidogenic protein is present or deposited within the central nervous system of a subject. Amyloid proteins known to cause cerebral amyloidosis include, but are not limited to, amyloid-beta, prion protein, cystatin C, synuclein, tau, ABri, and ADan. Conditions resulting from, or involving cerebral amyloidosis that are amenable to treatment in accordance with the methods of the present invention include, but are not limited to, Alzheimer disease, Down syndrome, diffuse Lewy body disease, fronto-temporal dementia, Parkinson's disease, hereditary cerebral hemorrhage with amyloidosis, kuru, Creutzfeldt-Jakob disease, Gerstmann-Straussler-Scheinker syndrome, fatal familial insomnia, British familial dementia, and Danish familial dementia.

Another aspect of the present invention is directed to a method of preventing or treating AD in a subject. This method comprises selecting a subject susceptible to or afflicted with AD and administering to the selected subject an agent that stimulates the innate immune system of the subject under conditions effective to prevent or treat AD.

As used herein, "subject" refers to any animal that exhibits amyloid deposition, cerebral amyloidosis, or AD. Preferably, the subject is a mammal. Exemplary mammalian subjects include, without limitation, humans, non-human primates, dogs, cats, rodents (e.g., mouse, rat, guinea pig), horses, cattle and cows, sheep, and pigs.

In accordance with the methods of the present invention, stimulating the innate immune response in a subject can involve activating any component of the innate immune system (i.e. phagocytic cells, including dendritic cells, complement factors, etc.) using appropriate effector molecules. Examples of effector molecules for stimulating the innate immune system are disclosed in U.S. Patent Publication Nos. 20070190533 to Hanocock et al. and 20060135459 to Epstein, which are hereby incorporated by reference in their entirety.

In one embodiment of the present invention, the innate immune response of an affected subject is stimulated by induction of one or more members of the Toll-like receptor (TLR) family or other TLR-interleukin-1 receptor (TIR) domain receptors, which share sequence homology at the intracellular signaling domain allowing them to activate similar intracellular signaling pathways. In a preferred embodiment, TLR9 signaling is activated.

In one aspect of the present invention, TLR9 signaling is induced by an immunomodulatory oligodeoxynucleotide (ODN). TLR9 functions, naturally, by specifically binding nucleic acids that contain unmethylated cytosine-guanosine (CpG) sequences, which are commonly found in prokaryotic and viral genomes but are underrepresented in eukaryotic genomes (Krieg et al., "CpG Motifs in Bacterial DNA and Their Immune Effects," *Annu Rev Immunol* 20:709-760 (2002), which is hereby incorporated by reference in its entirety). Unless specifically designed to be methylated, CpG-containing DNA oligodeoxynucleotides (ODNs) synthesized in the laboratory or purchased from commercial suppliers are unmethylated, and, therefore, can be utilized to activate TLR9.

In a particular aspect, ODNs useful in carrying out the methods of the present invention bear at least one CpG dinucleotide or CpG-like motif. In another aspect, the ODN contains two or more CpG dinucleotide motifs separated by at least three nucleotides. Internucleotide linkages of the ODN are typically either phosphorodithioate bonds (phosphorothioate backbone) or phosphodiester bonds (phosphoester backbone). Backbones can be mixed in that an ODN may have one type of backbone in one place and another type in another place.

There are three different classes of TLR9 stimulator CpG ODNs, i.e. class A, B, and C, each of which can be used in the methods of the present invention. Each class of CpG ODN leads to slightly different outcomes with regard to cells activated and signaling pathways stimulated. (Krieg, "Therapeutic Potential of Toll-like Receptor 9 Activation," Nature Rev Drug Discov 5:471-84 (2006), which is hereby incorporated by reference in its entirety). Type A CpG ODNs are characterized by a phosphodiester central CpG-containing palindromic motif and a phosphorothioate 3' poly-G string. They may induce high IFN-α production from plasmacytoid dendritic cells (pDC) but are typically weak stimulators of TLR9-dependent NF-κB signaling. Type B CpG ODNs contain a full phosphorothioate backbone with one or more CpG dinucleotides. They directly stimulate phagocyte activation, DC maturation, and B cell proliferation, but weakly stimulate IFN-α secretion. Type C CpG ODNs combine features of both type A and type B. They contain a complete phosphorothioate backbone and a CpG containing palindromic motif. Type C CpG ODNs induce strong IFN-α production from pDC and B-cell stimulation.

Synthetic ODNs useful for stimulating TLR9 activation are readily known in the art, including those described below and those disclosed by U.S. Pat. Nos. 6,207,646 and 6,239,116, to Krieg; U.S. Patent Publication Nos. 20040198680, 20080009455, and 20070224210 to Krieg; and U.S. Patent Publication No. 20060135459 to Epstein, which are hereby incorporated by reference in their entirety. Various CpG DNA TLR9 agonists that are currently in clinical trials, many of which have already proven to be safe in humans and rodents (Krieg, "Therapeutic Potential of Toll-like Receptor 9 Activation," Nature Rev Drug Discov 5:471-84 (2006); Crack et al., "Toll-like Receptors in the Brain and Their Potential Roles in Neuropathology," Immunol Cell Biol 85:476-80 (2007), which are hereby incorporated by reference in their entirety), would be particularly useful for carrying out the methods of the present invention. Specifically, CpG ODNs IMO-2055 and IMO-2125, developed as lead compounds for the treatment of cancer and hepatitis C, respectively, (Agrawal and Kandimalla, "Synthetic Agonists of Toll-like Receptors 7, 8, and 9," Biochem Soc Trans 35:1461-1467 (2007), which is hereby incorporated by reference in its entirety), would be particularly useful in the methods of the present invention. Additionally, CpG 7909 (TCG TCG TTT TGT CGT TTT GTC GTT; (SEQ ID NO: 8)) or analogs thereof, described in U.S. Patent Publication Nos. 2007012932 and 20060287263 both to Davis et al., which are hereby incorporated by reference in their entirety, or ODN 1018 ISS (TGACTGTGAACGTTCGAGATGA; (SEQ ID NO:9)) described in U.S. Patent Publication No. 20050175630 to Raz et al., which is hereby incorporated by reference in its entirety, would also be useful in carrying out the methods of the present invention.

Additional CpG ODNs useful for carrying out the methods of the present invention include ODN 1826, a class B CpG ODN containing two CpG sequences and a complete phosphorothioate backbone (Spinner et al., "CpG Oligodeoxynucleotide-Enhanced Humoral Immune Response and Production of Antibodies to Prion Protein PrPSc in Mice Immunized with 139A Scrapic-Associated Fibrils," J Leukoc Biol 14:36-43 (2007), which is hereby incorporated by reference in its entirety). ODN 1826 is available commercially, for example, from Oligos Etc. (Wilsonville, Oreg.) and Integrated DNA Technologies (Coralville, Iowa), or readily made from companies including Invivogen (San Diego, Calif.) and Axxora/Alexis Biochemicals (San Diego, Calif.). Other useful ODNs include, but are not limited to: ODN 1826 (5'-TCC ATG ACG TTC CTG ACG TT-3') (SEQ ID NO: 1); ODN 1631 (5'-CGC GCG CGC GCG CGC GCG CG-3') (SEQ ID NO: 2); ODN 1984 (5'-TCC ATG CCG TTC CTG CCG TT-3') (SEQ ID NO: 3); ODN 2010 (5'-GCG GCG GGC GGC GCG CGC CC-3') (SEQ ID NO: 4); CpG 1758 (5'-CTC CCA GCG TGC GCC AT-3') (SEQ ID NO: 5); CpG 2006 (5'-TCG TCG TTT TGT CGT TTT GTC GTT-3') (SEQ ID NO: 6); CpG 1668 (5'-TCC ATG ACG TTC CTG ATG CT-3') (SEQ ID NO: 7); and the like, and modifications thereof.

Alternatively, CpG oligonucleotides, useful for carrying out the methods of the present invention, may include the ODNs mentioned above with inconsequential nucleotide deletions or additions thereto. Indeed, methods for enhancing TLR9 activation and signaling by modifying neutralizing and stimulatory CpGs present within a particular ODN are disclosed by U.S. Pat. Nos. 6,339,068 and 6,194,388 to Krieg; Agrawal and Kandimalla, "Synthetic Agonists of Toll-like Receptors 7, 8, and 9," Biochem. Soc. Trans. 35:1461-1467 (2007), which are hereby incorporated by reference in their entirety. ODNs may have modified base structures, including even complete replacement of bases with moieties such as hypoxanthine or 6-thioguanine (Jurk et al., "Structure-Activity Relationship Studies on the Immune Stimulatory Effects of Base-Modified CpG Toll-like Receptor 9 Agonists," Chem Med Chem 1:1007-1014 (2006), which is hereby incorporated by reference in its entirety) or other purine nucleobases such as 7-deaza-dG, $N^1$-Me-dG, 2-amino-D-purine, nebularine, 2-amino-dA, 7-deaza-D-xanthine, K-base, and dI (Agrawal and Kandimalla, "Synthetic Agonists of Toll-like Receptors 7, 8 and 9," Biochem Soc Trans 35:1461-1467 (2007), which is hereby incorporated by reference in its entirety). Likewise various pyrimidine analogues, such as 5-OH-dC, dU, dP, 1-(2'-deoxy-β-D-ribofuranosyl)-2-oxo-7-deaza-8-methyl-purine, $N^3$-Me-dC, and $N^4$-Et-dC can replace the cytosine base (Agrawal and Kandimalla, "Synthetic Agonists of Toll-like Receptors 7, 8 and 9," Biochem Soc Trans 35:1461-1467 (2007), which is hereby incorporated by reference in its entirety).

Additional modification to ODNs to enhance stimulatory activity include modifications to the sequences flanking the CpG motifs. TLR9 agonist ODNs containing methylphosphonate linkages, 2'-alkyl or 3'-deoxy or -alkyl ribonucleosides, non-nucleotide linkers or abasic nucleotides in the sequences flanking the CpG motifs have significantly enhanced immunostimulatory activity (Agrawal and Kandimalla, "Synthetic Agonists of Toll-like Receptors 7, 8 and 9," Biochem Soc Trans 35:1461-1467 (2007), which is hereby incorporated by reference in its entirety). Modifications to the phosphodiester backbone of the ODN can also enhance its immunostimulatory activity. For example, introduction of a sulfur atom on the internucleotide phosphodiester bond results in the formation of Rp and Sp diastereoisomers with the Rp diastereomer eliciting a stronger TLR9 response.

It is known in the art that CpG ODN stimulation of TLR9 requires a free 5'end. Therefore, agonists comprising two CpG ODN versions in a hybridized complex may be administered together (Agrawal and Kandimalla, "Synthetic Agonists of Toll-like Receptors 7, 8 and 9," Biochem Soc Trans 35:1461-1467 (2007), which is hereby incorporated by reference in its entirety).

In addition to CpG ODNs, CpG oligoribonucleotides (ORN) and oligodeoxyribonucleotides containing unmethylated CpG motifs act as TLR9 agonists and can be used for carrying out the methods of the present invention. Exemplary CpG ORNs include those disclosed by Sugiyama et al., "CpG RNA: Identification of Novel Single-Stranded RNA that Stimulates Human CD14+CD11c+ Monocytes," *J Immunology* 174:2273-79 (2005) and U.S. Patent Publication No. 20050256073 to Lipford et al., which are hereby incorporated by reference in their entirety. Alternatively, RNA and DNA non-CpG TLR9 agonists can also be used in the methods of the present invention. Suitable non-CpG nucleic acid TLR agonists have been described (Lan et al., "Stabilized Immune Modulatory RNA Compounds as Agonists of Toll-Like Receptors 7 and 8," *Proc Natl Acad Sci USA* 104(34): 13750-5 (2007); Agrawal et al., "Synthetic Agonists of Toll-Like Receptors 7, 8, and 9," *Biochem Soc Trans* 35:1461-7 (2007), which are hereby incorporated by reference in their entirety).

Methods for producing phosphorothioate oligonucleotides or phosphorodithioate oligonuclotides are well-known in the art. The CpG ODNs may be synthesized by any method known in the art. Conveniently, such ODNs may be synthesized by an automated synthesizer. Additionally, CpG ODNs are available commercially from, for example, Cell Sciences (Canton, Mass.), Invivogen (San Diego, Calif.), and Axxora, LLC (San Diego, Calif.).

The methods of the present invention are not limited to the CpG ODNs disclosed above. Methods for identifying new CpG ODNs, specifically those that activate the TLR9 are readily known in the art (U.S. Patent Publication No. 20060127884 to Latz et al., which is hereby incorporated by reference in its entirety) and can be utilized to identify additional CpG ODN sequences with utility in the methods of the present invention.

In another embodiment of the present invention, TLR9 signaling is induced by small molecule agonists. Suitable synthetic small molecule oligonucleotide based TLR9 agonists are described in U.S. Published Patent Application No. 20080292648 to Ekambar et al., which is hereby incorporated by reference in its entirety. Other small synthetic DNA and RNA TLR9 agonists include those described by Agrawal et al., "Synthetic Agonists of Toll-like Receptors 7,8 and 9," *Biochem Soc Trans* 35:1461-1467 (2007), which is hereby incorporated by reference in its entirety. In addition small molecular libraries, such as that disclosed by Li et al., "Styryl Based In Vivo Imaging Agents for β-amyloid Plaques," *ChemBioChem* 8(14): 1679-1687, 2007, which is hereby incorporated by reference in its entirety, can be screened for TLR9 agonists useful in the methods of the present invention.

A further aspect of the present invention relates to a composition useful for the stimulation of the innate immune system of a subject exhibiting symptoms associated with amyloid deposition. This composition includes an oligonucleotide bearing at least one CpG motif and a pharmaceutically effective carrier.

Another aspect of the present invention relates to a pharmaceutical composition for preventing or reducing amyloid deposition, preventing or treating cerebral amyloidosis, or preventing or treating Alzheimer's disease. The pharmaceutical composition contains an agent capable of stimulating the innate immune system of a subject and a pharmaceutically effective carrier. In a preferred embodiment, the agent induces TLR signaling and is a CpG ODN.

The CpG ODN of the compositions of the present invention can be any of those disclosed above.

The CpG stimulatory ODN can be administered directly to the subject. Alternatively, the CpG ODN can be administered in conjunction with a nucleic acid delivery complex. The nucleic acid delivery complex is a nucleic acid molecule associated with a targeting means (e.g. a molecule that results in higher affinity binding to target cell). Examples of nucleic acid delivery complexes include nucleic acids associated with a sterol (e.g. cholesterol), a lipid (e.g. a cationic lipid, virosome or liposomes), or a target cell specific binding agent (e.g. a ligand recognized by a target cell specific receptor). Preferred complexes may be sufficiently stable in vivo to prevent significant uncoupling prior to internalization by the target cell. However, the complex can be cleavable under appropriate conditions within the cell so that the oligonucleotide is released in a functional form.

In practicing the method of the present invention, the composition can be administered using any method standard in the art. The composition can be administered orally, intradermally, intramuscularly, intraperitoneally, intravenously, subcutaneously, intranasally, intrathecally, or intracerebrally. The composition of the present invention may be administered alone or with suitable pharmaceutical carriers, and can be in solid or liquid form, such as tablets, capsules, powders, solutions, suspensions, or emulsions.

A CpG ODN, may be formulated into a "vaccine," and administered in free solution, or together with free antigen, or covalently conjugated to an antigen, or formulated with a carrier such as aluminum hydroxide, or combined with a saponin. The CpG ODN may be combined with a carrier, such as a particulate carrier like metallic salt particles, emulsions, polymers, liposomes, or immunostimulating complex adjuvants (ISCOMs) (see e.g., U.S. Pat. No. 6,544,518 to Laus et al., which is hereby incorporated by reference in its entirety).

The agent of the present invention may be orally administered, for example, with an inert diluent, or with an assimilable edible carrier, or it may be enclosed in hard or soft shell capsules, or it may be compressed into tablets, or they may be incorporated directly with the food of the diet. CpG ODNs may also be administered in a time release manner incorporated within such devices as time-release capsules or nanotubes. Such devices afford flexibility relative to time and dosage. For oral therapeutic administration, the agent of the present invention may be incorporated with excipients and used in the form of tablets, capsules, elixirs, suspensions, syrups, and the like. Such compositions and preparations should contain at least 0.1% of the agent, although lower concentrations may be effective and indeed optimal. The percentage of the agent in these compositions may, of course, be varied and may conveniently be between about 2% to about 60% of the weight of the unit. The amount of the agent of the present invention in such therapeutically useful compositions is such that a suitable dosage will be obtained.

Also specifically contemplated are oral dosage forms of the above ODN component or components. The ODN component or components may be chemically modified so that oral delivery of the derivative is efficacious. Generally, the chemical modification contemplated is the attachment of at least one moiety to the component molecule itself, where said moiety permits (a) inhibition of proteolysis; and (b) uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. (Abuchowski and Davis, "Soluble Polymer-Enzyme Adducts" in *Enzymes as Drugs* 367-83 (Hocenberg and Roberts eds., 1981), which is hereby incorporated by reference in it entirety). Other polymers that could be used are poly-1,3-dioxolane and poly-1, 3,6-trioxocane. Preferred for pharmaceutical usage, as indicated above, are polyethylene glycol moieties.

The tablets, capsules, and the like may also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, sucralose, or saccharin. When the dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar, or both. A syrup may contain, in addition to active ingredient, sucrose as a sweetening agent, methyl and propylparabens as preservatives, a dye, and flavoring such as cherry or orange flavor.

The agent of the present invention may also be administered parenterally. Solutions or suspensions of the agent can be prepared in water suitably mixed with a surfactant such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Intraperitoneal, intrathecal, or intracerebral administration of CpG ODNs can also be achieved using infusion pump devices such as those described by Medtronic, Northridge, Calif. Such devices allow continuous infusion of desired compounds avoiding multiple injections and multiple manipulations.

In addition to the formulations described previously, the compounds may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt The agent of the present invention may also be administered directly to the airways in the form of an aerosol. For use as aerosols, the agent of the present invention in solution or suspension may be packaged in a pressurized aerosol container together with suitable propellants, for example, hydrocarbon propellants like propane, butane, or isobutane with conventional adjuvants. The agent of the present invention also may be administered in a non-pressurized form such as in a nebulizer or atomizer.

Effective doses of the compositions of the present invention, for the treatment of a subject having amyloid deposits, cerebral amyloidosis, or AD vary depending upon many different factors, including means of administration, target site, physiological state of the patient, other medications administered, physical state of the patient relative to other medical complications, and whether treatment is prophylactic or therapeutic. Treatment dosages need to be titrated to optimize safety and efficacy. The amount of CpG ODN depends on whether an additional adjuvant is also administered, with higher dosages being required in the absence of an additional adjuvant. Subject doses of the CpG ODNs described herein for mucosal or local delivery typically range from about 0.1 µg to 50 mg per administration, which depending on the application could be given daily, weekly, or monthly and any other amount of time therebetween. More typically mucosal or local doses range from about 10 µg to 10 mg per administration, and optionally from about 100 µg to 1 mg, with 2-4 administrations being spaced days or weeks apart. More typically, immune stimulant doses range from 1 µg to 10 mg per administration, and most typically 101 g to 1 mg, with daily or weekly administrations. Doses of the compounds described herein for parenteral delivery e.g., for inducing an innate immune response, or in specialized delivery vehicles typically range from about 0.1 µg to 10 mg per administration, which depending on the application could be given daily, weekly, or monthly and any other amount of time therebetween. More typically parenteral doses for these purposes range from about 10 µg to 5 mg per administration, and most typically from about 100 µg to 1 mg, with 2-4 administrations being spaced days or weeks apart. In some embodiments, however, parenteral doses for these purposes may be used in a range of 5 to 10,000 times higher than the typical doses described above The following examples illustrate various methods for compositions in the treatment method of the invention. The examples are intended to illustrate, but in no way limit, the scope of the invention.

EXAMPLES

Example 1—Animals and Treatment

The present examples were performed in the heterozygous Tg2576 APP mouse model (Hsiao et al., "Correlative Memory Deficits, Abeta Elevation, and Amyloid Plaques in Transgenic Mice," *Science* 274:99-102 (1996), which is hereby incorporated by reference in its entirety). These mice overexpress a 695 amino acid splice form (Swedish mutation K670N M671I) of the human amyloid β precursor protein (APP) and show rapid increase in Aβ levels at approximately six months of age with Aβ deposition developing in the following months, although extensive amyloid burden is usually not observed before their second year. The Tg2576 mice used were bred internally on a C57B6 X SJL F1 background. These mice carry the recessive retinal degeneration (rd) mutation due to the SJL strain. Mice homozygous for the mutation have impaired vision and were excluded from this study. Also to reduce any confounds in the behavioral testing due to impaired vision, albino mice were excluded from this study. The animals were maintained on a 12-hour light-dark cycle. All mouse care and experimental procedures were approved by the Institutional Animal Care and Use Committee at the New York University School of Medicine.

Female Tg2576 mice were injected with either the TLR9 agonist CpG oligodeoxynucleotide (ODN) 1826 (5'-TCC ATG ACG TTC CTG ACG TT-3') (SEQ ID NO: 1; CpG motifs in bold) (2.5 mg/kg body weight, ~63 μg) or vehicle (HBSS) beginning at the age of six weeks, and once a month thereafter for a total of fourteen injections. Unless specifically designed to be methylated, CpG-containing ODNs synthesized in the laboratory or purchased from suppliers are unmethylated, and therefore can be used to activate TLR9. CpG ODN 1826, with a complete phosphorothioate backbone, was purchased from Integrated DNA Technologies. The dose of CpG ODN 1826 was the same dose shown to stimulate the innate immune system in mice to enhance a response to 139A scrapie associated fibrils (Spinner et al., "CpG Oligodeoxynucleotide-Enhanced Humoral Immune Response and Production of Antibodies to Prior Protein in PrPSc in Mice Immunized with 139A Scrapie-Associated Fibrils," *J Leuko Biol* 81(6):1374-85 (2007), which is hereby incorporated by reference in its entirety). Controls were non-transgenic C57BL/6×SJL mice injected with HBSS on the same schedule. During the treatment, animals were monitored closely for signs of toxicity, and after sacrifice their organs were examined for any signs of pathology. No toxicity was evident in the CpG ODN-treated group.

Example 2—Behavioral Testing

Prior to cognitive testing, the mice were subjected to locomotor activity test. This measurement of locomotor behavioral was performed to verify that any CpG ODN treatment-related effects observed in the cognitive tasks could not be explained by differences in locomotor activity. The behavioral study was performed in twenty four CpG ODN-treated Tg animals. Twenty age-matched, vehicle-treated Tg mice and twenty five non-Tg, age-matched littermates were used as controls.

Exploratory locomotor activity was recorded in a circular open field activity chamber measuring (70 cm×70 cm). A video camera mounted above the chamber automatically recorded horizontal movements in the open field in each dimension (i.e., x, y, and two z planes). Total distance was measured in centimeters (cm) traveled and is defined as sequential movement interruptions of the animal measured relative to the background. The duration of the behavior was timed for 15 min. Results are reported based on distance traveled (cm), mean resting time, and velocity (average and maximum) of the animal.

Spatial learning (working memory) was evaluated using an eight-arm radial maze with a water well at the end of each arm, as described previously (Sadowski et al., "Blocking the Apolipoprotein E/amyloid-beta Interaction as a Potential Therapeutic Approach for Alzheimer's Disease," *Proc Nat'l Acad Sci USA* 103:18787-92 (2006); Sigurdsson et al., "An Attenuated Immune Response is Sufficient to Enhance Cognition in an Alzheimer's Disease Mouse Model Immunized with Amyloid-beta Derivatives," *J Neurosci* 24:6277-82 (2004), which are hereby incorporated by reference in their entirety). Clear Plexiglas guillotine doors, operated by a remote pulley system, controlled access to the arms from a central area from which the animals entered and exited the apparatus. After 3 to 4 days of adaptation, water-restricted mice (2 h daily access to water) were given one training session per day for twelve consecutive days. For each session, all arms were baited with 0.1% saccharine solution, and animals were permitted to enter all arms until the eight rewards had been consumed. The number of errors (entries to previously visited arms) and time to complete each session were recorded. The behavioral testing was performed by an individual blinded to the animal's treatment status.

Example 3—Autoantibody Response

The autoantibody levels were determined by 1:200 dilutions of plasma using ELISA as described previously in which 0.5 μg per well of the Aβ40 or Aβ42 peptide was coated onto microtiter wells (Immulon 2HB; Thermo Electron Corp., Milford, Mass.) (Sadowski et al., "Blocking the Apolipoprotein E/Amyloid-beta Interaction as a Potential Therapeutic Approach for Alzheimer's Disease," *Proc Nat'l Acad Sci USA* 103:18787-92 (2006), which is hereby incorporated by reference in its entirety). The antibodies in plasma were detected by a goat anti-mouse IgG linked to a horseradish peroxidase conjugate (Catalog #A8786, Sigma-Aldrich, St. Louis, Mo.) at 1:3000 dilution. Tetramethyl benzidine (TMB) (Pierce, Rockford, Ill.) was the substrate.

Example 4—Histological Studies

Following completion of behavioral testing at 17 months of age, the mice were anesthetized with sodium pentobarbital (150 mg/kg, i.p.) and perfused transaortically with 0.1M PBS, pH 7.4. The brains were removed and the right hemisphere was immersion-fixed in periodate-lysine-paraformaldehyde (PLP), whereas the left hemisphere was snap-frozen for measurements of Aβ oligomers and Aβ levels.

After fixation, the brains were placed in a solution of 2% DMSO/20% glycerol in PBS and stored until sectioned. Serial coronal brain sections (40 μm) were cut and eight series of sections at 0.32 mm intervals saved for histological analysis using: (1) 6E10/4G8, (2) Thioflavin-S, (3) anti-GFAP, (4) anti-CD11b, and (5) anti-CD45 antibodies, as described previously (Sadowski et al., "Blocking the Apolipoprotein E/Amyloid-beta Interaction as a Potential Therapeutic Approach for Alzheimer's Disease," *Proc Nat'l Acad Sci USA* 103:18787-92 (2006), which are hereby incorporated by reference in its entirety). Aβ deposits were stained either with a mixture of monoclonal antibodies 6E10/4G8 or Thioflavin-S for fibrillar amyloid. GFAP is a component of the glial intermediate filaments that forms part of the cytoskeleton and is found predominantly in astrocytes. The two different markers used to identify microglia include CD45 (protein-thyrosine phosphatase) and CD11b (member of β-integrin family of adhesion molecules; also known as MAC-1 or complement receptor 3 (CR3). Both CD45 and CD11b are commonly used as markers for microglial activation at the earliest and later stages of plaque development, respectively. The remaining series were placed in ethylene glycol cryoprotectant (30% sucrose/30% ethylene glycol in 0.1 mol/L phosphate buffer) and stored at −20° C. until used.

Immunostaining with antibodies, 6E10/4G8 (Covance/Signet Laboratories, Dedham, Mass.) to Aβ, or antibodies to GFAP, CD45, or CD11b, was performed as described previously (Sadowski et al., "Blocking the Apolipoprotein E/Amyloid-beta Interaction as a Potential Therapeutic Approach for Alzheimer's Disease," *Proc Nat'l Acad Sci USA* 103:18787-92 (2006), which is hereby incorporated by reference in its entirety). Briefly, free-floating sections were incubated with 6E10/4G8, both monoclonal anti-Aβ antibodies, at a 1:1000 dilution for three hours. A mouse-on-mouse immunodetection kit (Vector Labs, Burlingame, Calif.) was used with the biotinylated anti-mouse IgG secondary antibody reacted for 1 h at a 1:1000 dilution. Antibody staining was revealed with 3,3'-diaminobenzidine (DAB; Sigma-Aldrich) and nickel ammonium sulfate intensification. GFAP (polyclonal, 1:1000; 3h, Dako, Denmark) was performed with the primary antibody diluent composed of 0.3% Triton X-100, 0.1% sodium azide, 0.01% bacitracin, 1% bovine serum albumin, and 10% normal goat serum in PBS, and the secondary biotinylated goat anti-rabbit antibody (Vector Labs) was reacted for 1h at 1:1000 dilution. CD45 (rat anti-mouse, 1:1000; 3 h (Serotec, Raleigh, N.C.)), and CD11b immunohistochemistry (rat anti-mouse 1:500; 3 h, Serotec) were performed similarly to that for GFAP staining except that the secondary antibody was a goat anti-rat (Vector Labs) diluted 1:1000. Selected series were double-stained using Thioflavin-S and anti-CD45. Thioflavin-S staining was performed on mounted sections, as published previously (Sadowski et al., "Blocking the Apolipoprotein E/Amyloid-beta Interaction as a Potential Therapeutic Approach for Alzheimer's Disease," *Proc Nat'l Acad Sci USA* 103:18787-92 (2006), which is hereby incorporated by reference in its entirety). Perl's Prussion blue staining for ferric iron in hemosiderin (degradation product of hemoglobin) was performed on another set of sections to detect cerebral bleeding. Equally spaced sections were mounted and stained in a solution containing 10% potassium ferrocyanide and 20% hydrochloric acid for 45 min. For the hemosiderin stain, 10-15 sections were examined and the average number of iron positive profiles per section was calculated.

Example 5—Image Analysis

Immunostained tissue sections were quantified with a Bioquant stereology semi-automated image analysis system (R&M Biometrics Inc., Nashville, Tenn.) using random unbiased hierarchical sampling scheme, as published previously (Sadowski et al., "Blocking the Apolipoprotein E/Amyloid-beta Interaction as a Potential Therapeutic Approach for Alzheimer's Disease," *Proc Nat'l Acad Sci USA* 103:18787-92 (2006); Sigurdsson et al., "An Attenuated Immune Response is Sufficient to Enhance Cognition in an Alzheimer's Disease Mouse Model Immunized with Amyloid-beta Derivatives," *J Neurosci* 24:6277-82 (2004), which are hereby incorporated by reference in their entirety).

Seven sections were analyzed per animal. All procedures were performed by an individual blinded to the experimental conditions of the study. Total Aβ burden (defined as the percentage of test area occupied by AP) was quantified in the cortex and in the hippocampus on coronal plane sections stained with the monoclonal antibodies 6E10/4G8. Intensification with nickel ammonium sulfate resulted in black Aβ with minimal background staining that facilitated threshold detection. The cortical area was dorsomedial from the cingulate cortex and extended ventrolaterally to the rhinal fissure within the right hemisphere. Test areas (640 μm×480 μm) were randomly selected by applying a grid (800 μm×800 μm) over the traced contour. Hippocampal measurements (600 μm×600 μm) were performed in a similar manner as the cortical analysis (Sadowski et al., "Blocking the Apolipoprotein E/Amyloid-beta Interaction as a Potential Therapeutic Approach for Alzheimer's Disease," *Proc Nat'l Acad Sci USA* 103:18787-92 (2006); Sigurdsson et al., "An Attenuated Immune Response is Sufficient to Enhance Cognition in an Alzheimer's Disease Mouse Model Immunized with Amyloid-beta Derivatives," *J Neurosci* 24:6277-82 (2004), which are hereby incorporated by reference in their entirety. Total fibrillar Aβ3 burden (parenchymal and vascular) and cerebral amyloid angiopathy (CAA) burden (Aβ burden in the vasculature) were evaluated separately in sections stained with Thioflavin-S, using methods described previously (Asuni et al., "Vaccination of Alzheimer's Model Mice with Abeta Derivative in Alum Adjuvant Reduces Abeta Burden without Microhemorrages," *Eur J Neurosci* 24(9):2530-42 (2006); Sadowski et al., "Blocking the Apolipoprotein E/Amyloid-Beta Interaction as a Potential Therapeutic Approach for Alzheimer's Disease," *Proc Nat'l Acad Sci USA* 103(49): 18787-92 (2006), which are hereby incorporated by reference in their entirety). The CD45 microglia burden (the percentage of area in the measurement field occupied by CD45 immunoreactive microglia) was quantified in an analogous manner to that used to measure the Aβ burden.

Example 6—Rating of Microgliosis

The assessment of the CD11b immunostained sections was based on a semiquantitative analysis of the extent of microgliosis (0, a few resting microglia; 1, a few ramified and/or phagocytic microglia; 2, moderate number of ramified/phagocytic microglia; 3, numerous ramified/phagocytic microglia) (Sigurdsson et al., "Enhanced Cognition with a Reduced Immune Response in an AD Mouse Model Immunized with Aβ Derivatives," *J Neurosci* 24: 6277-6282 (2004); Asuni et al., "Aβ Derivative Vaccination in Alum Adjuvant Prevents Amyloid Deposition and Does Not Cause Brain Microhemorrhages in Alzheimer's Model Mice," *Eur J Neurosci* 24: 2530-2542 (2006), which are hereby incorporated by reference in their entirety).

Example 7—Rating of Astrocytosis

Reactive astrocytosis was rated on a scale of 0.5-3. The rating was based on a semiquantitative analysis of the extent of GFAP immunoreactivity (number of GFAP immunoreactive cells and complexity of astrocytic branching) (Sigurdsson et al., "Enhanced Cognition with a Reduced Immune Response in an AD Mouse Model Immunized with Aβ Derivatives," *J Neurosci* 24: 6277-6282 (2004); Asuni et al., "Aβ Derivative Vaccination in Alum Adjuvant Prevents Amyloid Deposition and Does Not Cause Brain Microhemorrhages in Alzheimer's Model Mice," *Eur J Neurosci* 24: 2530-2542 (2006), which are hereby incorporated by reference in their entirety).

Example 8—Tissue Homogenization and Sandwich ELISA for Aβ Levels

Before extraction of Aβ from brain tissue, 10% (w/v) homogenates were prepared in tissue homogenization buffer (20 mM Tris base, pH 7.4, 250 mM sucrose, 1 mM EDTA, 1 mM EGTA) with 100 mM phenylmethylsulphonyl fluoride and protease inhibitors (protease inhibitors cocktail (Complete, Roche Diagnostic) plus pepstatin A) added immediately before homogenization, as previously published (Asuni et al., "Vaccination of Alzheimer's Model Mice with Abeta Derivative in Alum Adjuvant Reduces Abeta Burden without Microhemorrages," *Eur J Neurosci* 24(9):2530-42 (2006); Sadowski et al., "Blocking the Apolipoprotein E/Amyloid-Beta Interaction as a Potential Therapeutic Approach for Alzheimer's Disease," *Proc Natl Acad Sci USA* 103(49): 18787-92 (2006); Scholtzova et al., "Memantine Leads to Behavioral Improvement and Amyloid Reduction in Alzheimer's Disease Model Transgenic Mice as Shown by Micromagnetic Resonance Imaging," *J Neurosci Res* 86(12):2784-91 (2008), which are hereby incorporated by reference in their entirety). For extraction of soluble Aβ, brain homogenates were thoroughly mixed with an equal volume of 0.4% diethylamine (DEA)/100 mM NaCl, then spun at 135,000×g for 1 h at 4° C., and subsequently neutralized with ⅒ volume of 0.5 M Tris, pH 6.8. The samples were then aliquoted, flash-frozen on dry ice, and stored at −80° C. until loaded onto ELISA plates. Similarly for extraction of the total Aβ, homogenates (200 µl) were added to 440 µl of cold formic acid (FA) and sonicated for 1 min on ice. Subsequently, 400 µl of this solution was spun at 100,000×g for 1 h at 4° C. Then, 210 µl of the resulting supernatant was diluted into 4 ml of FA neutralization solution (1 M Tris base, 0.5 MNa2HPO4, 0.05% NaN3), aliquoted, flash-frozen on dry ice, and stored at −80° C. until used for Aβ measurements. The total and soluble Aβ levels were measured using a combination of mouse monoclonal antibody 6E10 (specific to an epitope present on amino acid residues 1-16 of Aβ) and two different rabbit polyclonal antibodies specific for Aβ40 (R162) and Aβ42 (R165), in a double-antibody sandwich ELISA as described previously (Sadowski et al., "Blocking the Apolipoprotein E/Amyloid-Beta Interaction as a Potential Therapeutic Approach for Alzheimer's Disease," *Proc Natl Acad Sci USA* 103(49): 18787-92 (2006), which is hereby incorporated by reference in its entirety). The optical density (OD) was measured at 450 nm. The relationship between OD and Aβ peptide concentration was determined by a four-parameter logistic log function. Nonlinear curve fitting was performed with the KinetiCalc program (Biotek Instruments) to convert OD of plasma to estimated concentrations. The assay was performed by an investigator blinded to group assignment. The levels of Aβ species are presented as µg of Aβ per gram of wet brain, taking into account dilution factors introduced by multiple steps throughout the assay (brain homogenization and extraction procedures).

Example 9—Western Blot Analysis of Aβ Oligomers

For Western immunoblot analysis, 10% (w/v) brain homogenates were centrifuged at 25,000×g for 10 min at 4° C., and the supernatants were transferred to clean tubes and stored as previously described (Sadowski et al., "Blocking the Apolipoprotein E/Amyloid-Beta Interaction as a Potential Therapeutic Approach for Alzheimer's Disease," *Proc Natl Acad Sci USA* 103(49): 18787-92 (2006), which is hereby incorporated by reference in its entirety). The total protein concentration in the supernatant was determined using the Bicinchoninic acid assay (BCA; Pierce). Samples (40 µg of total protein), mixed with an equal volume of Tricine sample buffer, were electrophoresed on 12.5% Tris-tricine polyacrylamide gels (under nonreducing conditions) and transferred to nitrocellulose membranes. The blots were blocked with 5% nonfat dry milk in Tris-buffered saline Tween 20 (TBS-T) for 2 h at room temperature. Oligomer-specific A11 polyclonal antibody (Biosource) was diluted (1:1000) in 0.1% BSA/TBS-T and incubated with the blots for 2 h at room temperature. Bound antibody was visualized with horseradish peroxidase-conjugated goat anti-rabbit IgG (1:8000; 1 h, Pierce) and the ECL detection system (Pierce). The specificity of A11 staining was confirmed by probing the membrane with anti-Aβ monoclonal antibodies 6E10 or 4G8 (Sadowski et al., "Blocking the Apolipoprotein E/Amyloid-Beta Interaction as a Potential Therapeutic Approach for Alzheimer's Disease," *Proc Natl Acad Sci USA* 103(49): 18787-92 (2006), which is hereby incorporated by reference in its entirety). Densitometric analysis of A11 immunoreactive oligomer specific bands was performed with NIH ImageJ version 1.34 software.

Example 10—Statistical Analysis

Data from the radial arm maze were analyzed by two-way repeated-measures ANOVA followed by a Ncuman-Kculs post hoc test (Statistica, version 6.1, (StatSoft)). Differences between groups in amyloid burden, Aβ levels within the brain, levels of oligomers, CD45, CD11b activated microglia, and GFAP astrogliosis were analyzed using a Student's unpaired two-tailed t test. Assessment of brain microhemorrhages was analyzed using a one-tailed t test. Correlation was determined by calculating the Pearson r correlation coefficient. All data were analyzed with Graph Pad Prism 5 (San Diego, Calif.).

Example 11—Behavioral Studies

Figure 2:
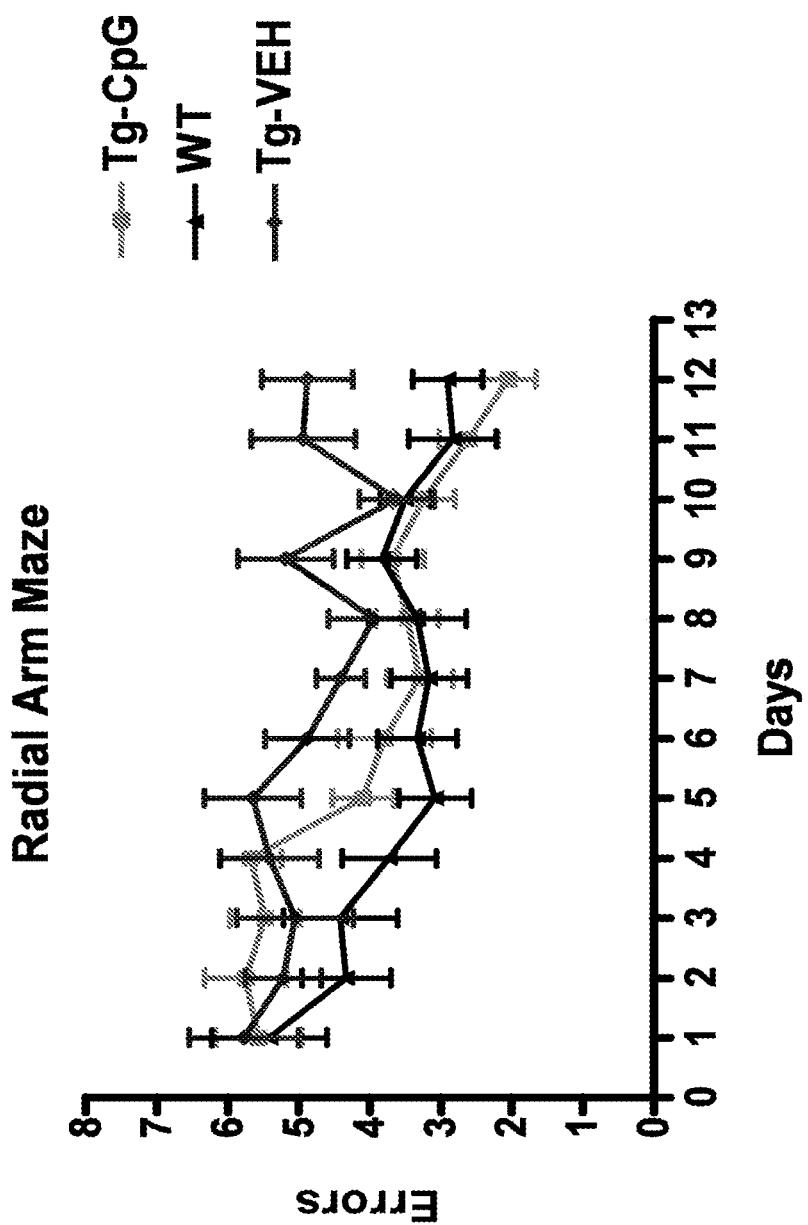
FIG. 2 is a graph showing data from radial arm maze test. Working memory improved with CpG ODN treatment in Tg2576 mice. Tg2576 mice treated with CpG ODN navigated the radial arm maze with significantly less errors than control Tg mice, and their performance was similar to that of their Wt age matched littermates (two-way repeated-measures ANOVA, group (treatment) effect, p=0.019; days effect, p<0.0001; interaction (group vs days), p=0.144, Newman-Keuls multiple comparison post hoc testing showed Tg-CpG vs Tg-vehicle, p=0.026; Tg-vehicle vs Wt, p=0.039; Tg-CpG vs Wt, p=0.814).

After treatment, at the age of sixteen months, mice were subjected to behavioral testing. The behavioral analysis consisted of both a cognitive assessment as well as measurements of exploratory locomotor activity. The latter test was included to verify that cognitive performance was not influenced by locomotor abnormalities. No statistical differences between groups were discerned in any of the locomotor parameters measured (FIGS. 1A-D). In addition to locomotor evaluation the mice underwent cognitive testing. Working memory was evaluated using the radial arm maze (FIG. 2). The overall performance (number of errors) of the mice differed significantly between transgenic groups (two-way repeated-measures ANOVA, group (treatment) effect, p=0.019; days effect, p<0.0001; interaction (group vs days), p=0.144). The CpG ODN-treated group was better at navigating the maze than the vehicle-treated Tg group. A significant difference was observed, with CpG ODN-treated mice performing comparably to Wt littermates (FIG. 2; Newman-Keuls post hoc test, Tg-CpG vs Tg-vehicle, p=0.026; Tg-CpG vs Wt, p=0.814). Vehicle-treated Tg mice made significantly more working memory errors than Wt animals (FIG. 2; Newman-Keuls post hoc test, p=0.039)

Example 12—Amyloid Burden

Mice were sacrificed at seventeen months of age after behavioral testing and their brains were processed for histology with subsequent stereological analysis as previously described (Sadowski et al., "Blocking the Apolipoprotein E/Amyloid-beta Interaction as a Potential Therapeutic Approach for Alzheimer's Disease," *Proc Nat'l Acad Sci USA* 103:18787-92 (2006); Asuni et al., "Vaccination of Alzheimer's Model Mice with Abeta Derivative in Alum Adjuvant Reduces Abeta Burden Without Microhemorrhages," *Eur J Neurosci* 24:476-80 (2006), which are hereby incorporated by reference in their entirety). Histological observation in APP Tg2576 mice indicated that CpG ODN-treated mice had fewer plaques compared to vehicle-treated Tg mice as visualized by Thioflavin-S staining (FIGS. 3C-D (cortex) and H-I (hippocampus)) and Aβ immunostaining (mAbs 6E10/4G8) (FIGS. 3A-B (cortex) and F-G (hippocampus)). Quantitative analysis of total amyloid burden was determined by stereological techniques, using random unbiased sampling on the immunostained serial sections evenly spaced along the entire-rostrocaudal axis of the brain. Peripheral administration of TLR9 agonist CpG ODN led to 66% (two-tailed t test, p=0.0001) reduction in total cortical amyloid burden (FIG. 3E) and 59% (p=0.002) reduction in hippocampal amyloid burden (FIG. 3J) compared to age-matched control Tg animals, which received vehicle only. Quantitative assessment of total cortical fibrillar amyloid burden also revealed a significant 74% (two-tailed t test, p=0.0001) reduction and a 78% reduction of the total fibrillar amyloid burden was observed in the hippocampus (two-tailed t test, p=0.0001). When analyzed separately, an 80% (p=0.0039) reduction in the CAA burden of cortical vessels was noted in the CpG ODN-treated animals (FIG. 4A-C). Brain microhemorrhages were detected in low numbers in Tg2576 mouse brain sections stained with Perl's stain. However, following treatment with CpG ODN a significant decrease in the extent of cerebral microhemorrhages was observed (FIG. 4D) (one-tailed t test, p=0.029).

Example 13—Assessment of Aβ Levels and Aβ Oligomers in the Brain

ELISA measurements revealed a statistically significant decrease in the levels of total (FA extracted) Aβ40 and Aβ42 by 59% (two-tailed t test, p=0.019) and 56% (p=0.026), respectively, after the CpG ODN treatment (FIG. 5A). The levels of soluble (DEA extracted) Aβ40 and Aβ42 fractions were significantly reduced by 75% (two-tailed t test, p=0.003) and 74% (p=0.0019), respectively, in CpG-treated mice (FIG. 5B). In addition, the measurements of total Aβ levels and total Aβ burden in the cortex (Aβ40, p<0.0001, $r^2$=0.75; Aβ42, p<0.0001, $r^2$=0.83) and hippocampus (Aβ40, p=0.0025, $r^2$=0.39; Aβ42, p=0.0014, $r^2$=0.43) correlated well and indicated a similar percentage reduction in the treated mice. No differences in the level of expression of human APP were found between CpG ODN-treated and vehicle-treated Tg mice. CpG ODN treatment is know to affect gene expression of numerous proteins, APP is not among these (Gao, et al., "Regulation of Gene Expression in Mouse Macrophages Stimulated with Bacterial CpG-DNA and Lipopolysaccharides," *J Leukoc Biol* 72:1234-45 (2002); Klaschik et al., "CpG-Mediated Changes in Gene Expression in Murine Spleen Cell Identified by Microarray Analysis," *Mol Immunol* 44(6):1095-104 (2007); Nagarajan et al., "Effects of CpG-B ODN on the Protein Expression Profile of Swine PBMC," *Vet Res* 38:795-808 (2007), which are hereby incorporated by reference in their entirety).

Soluble oligomeric Aβ ligands (also known as ADDLs) may account for memory loss and AD neuropathology, thus presenting a significant therapeutic target. The levels of pathogenic Aβ oligomers in the brain homogenates were assessed by Western blot using the A11 oligomer-specific antibody (FIG. 6A). CpG ODN treatment led to a significant decrease in the levels of A11 immunoreactive (56 kDa) oligomers (FIG. 6B; two-tailed t test, p=0.033). Furthermore, there was a correlation between the levels of 56 kDa Aβ assemblies and Aβ levels, with total Aβ levels correlating better than soluble Aβ levels (total Aβ40, p=0.0507, $r^2$=0.186; total Aβ42, p=0.047, $r^2$=−0.192; data not shown).

Example 14—Associated Histopathology

In addition to the analysis of Aβ burden in the parenchyma, the treatment effect of CpG ODN on microglial activation in APP Tg2576 mice was also evaluated. Subsequent immunohistochemical staining for the adhesion receptor CD11b, a well-established microglial and mononuclear phagocyte marker was performed (FIGS. 7A-B). The assessment of microglial marker CD11b was based on semiquantitative analysis of the extent of microgliosis. CpG ODN treatment resulted in reduction of overall cortical (FIG. 7C; two-tailed t test, p=0.0001) and hippocampal CD11b immunoreactivity. Although CD11b microglial expression was also found in non-Tg animals, staining intensity of CD11b marker was very low. In addition, the CD11b immunohistochemistry results were confirmed by staining the brains with another commonly used microglial and macrophage marker CD45, which is typically expressed in association with more mature plaques (Morgan et al., "Dynamic Complexity of the Microglial Activation Response in Transgenic Models of Amyloid Deposition: Implications for Alzheimer Therapeutics," *J Neuropathol Exp Neurol* 64:743-53 (2005), which is hereby incorporated by reference in its entirety). At seventeen-months of age, stereological quantitative analysis revealed an overall reduction in CD45 immunoreactivity. The CpG ODN-treated mice demonstrated a 71% reduction in cortical (FIG. 8A-C) and 73% reduction in hippocampal CD45 reactive microglia burden (FIG. 8 D-F). Despite reduction in CD11b and overall numbers of activated microglia labeled with anti-CD45 antibody, there was a significant increase in activated microglia around the few remaining plaques in the CpG ODN-treated mouse group. Semiquantification of CD45 immunoreactivity surrounding the plaques, measuring between 5 and 50 μm in diameter, was evaluated on a separate set of sections which were immunolabeled with CD45 antibody and Thioflavin S stained to visualize amyloid plaques (two-tailed t test, p=0.047) (FIGS. 9C-D, E). Astrocytes were detected using an antibody to the astrocyte-specific marker GFAP (FIGS. 10A-C). Semiquantitative rating of astroglial staining in cortex indicated fewer astrocytes in CpG ODN-treated group (Tg-CpG vs Tg-vehicle, p=0.006) (FIG. 10D).

In evaluating the efficacy of CpG ODN administration in AD mice model, stimulation of TLR9 signaling led to a remarkable reduction in amyloid burden which was paralleled by a reduction in the numbers of activated microglia and astrocytes. Furthermore, because antigen-presenting cells including microglia and dendritic cells are activated by TLR ligands, humoral immunity to Aβ may be induced.

To determine whether CpG ODN amyloid removal correlated with the production of antibody to Aβ species, the autoantibody response towards Aβ40 and Aβ42 was assessed periodically. No group differences were observed in the levels of autoantibodies in animals at 12 months of age. However, plasma obtained at the end of the study (at seventeen months) contained higher antibody levels against Aβ40 (FIG. 11A; p=0.017) and Aβ42 (FIG. 11B; p=0.09) in CpG ODN-treated group as compared to vehicle-treated controls.

As described herein, Type B CpG ODNs stimulate the innate immune system in AD model mice and reduced amyloid deposition, leading to behavioral improvements without inducing any toxicity. More specifically, the results indicate that stimulation of the TLR9 receptor by CpG ODN leads to a dramatic reduction of the amyloid burden in AD model mice. Specifically, there was a 66% reduction in cortical amyloid burden (*p=0.0001; two-tailed t-test) and a 59% reduction in hippocampal amyloid burden (p=0.002) (FIGS. 3E and J). This reduction of amyloid burden was associated with behavioral improvement as indicated by radial arm maze testing (FIG. 2). Behavioral studies verified that any differences between the groups could not be due to difference in the locomotor activity (FIGS. 1A-D), and had to be related to true differences in cognitive status. Behavioral improvements are likely related to reduction in 56 kDa Aβ oligomers (FIGS. 6A-B), which are linked more closely to functional deficits in AD model mice than fibrillar Aβ deposits.

Significantly, these studies clearly document that the immune stimulatory approach of the present embodiments is not associated with any central nervous system toxicity. The analysis of microglia brain reactivity showed a marked reduction, as assessed by CD11b and CD45 immunoreactivity, both in the cortex and hippocampus (FIGS. 7 and 8). In addition, CNS astrocytosis as assessed by GFAP immunoreactivity (FIG. 10), was also markedly reduced. Hence, there was no evidence of encephalitis in the brains of treated mice.

An additional potential complication of immunomodulation in the clearance of amyloid deposits is the occurrence of cerebral microhemorrhages. Several reports have shown an increase in microhemorrhages in different AD mouse models following passive intraperitoneal immunization with various monoclonal antibodies having high affinities for Aβ plaques and CAA (Pfeifer et al., "Cerebral Hemorrhage After Passive anti-Aβ Immunotherapy," *Science* 298:1379 (2002); Wilcock et al, "Passive Immunization Against Abeta in Ages APP-Transgenic Mice Reverses Cognitive Deficits and Depletes Parenchymal Amyloid Deposits in Spite of Increased Vascular Amyloid and Microhemorrhage," *J Neuroinflammation* 1:24 (2004), Racke et al., "Exacerbation of Cerebral Amyloid Angiopathy-Associated Microhemorrhages in Amyloid Precursor Protein Transgenic Mice by Immunotherapy is Dependent on Antibody Recognition of Deposited Forms of Amyloid beta," *J Neurosci* 25:629-36 (2005), which are hereby incorporated by reference in their entirety). Microhemorrhages following active immunization in animal models have been reported in at least one study (Wilcock et al., "Amyloid-beta Vaccination, But Not Nitro-Nonsteriodal Anti-Inflammatory Drug Treatment, Increases Vascular Amyloid and Microhemorrhages While Both Reduce Parenchymal Amyloid," *Neuroscience* 144:950-960 (2007), which is hereby incorporated by reference in its entirety). Early autopsies from the AN1792 trial indicated no clearance of vascular amyloid. In one of these cases numerous cortical bleeds, which are typically rare in AD patients, were evident suggesting that these may have been related to the immunization (Ferrer et al., "Neuropathology and Pathogenesis of Encephalitis Following Amyloid-beta Immunization in Alzheimer's Disease," *Brain Pathol* 14:11-20 (2004), which is hereby incorporated by reference in its entirety). This is an important issue since CAA is present in virtually all AD cases, with ~20% of AD patients having "severe" CAA (Jellinger K A, "Neuropathological Aspects of Alzheimer Disease, Parkinson Disease, and Frontotemporal Dementia," *Neurodegener Dis* 5:118-121 (2008), which is hereby incorporated by reference in its entirety). Furthermore, CAA is present in ~33% of cognitively normal elderly populations (Zhang-Nunes et al., "The Cerebral Beta-Amyloid Angiopathies: Hereditary and Sporadic," *Brain Pathol* 16:30-39 (2006), which is hereby incorporated by reference in its entirety). Hence it is important that in the present study, that stimulation of the innate immune system with CpG ODNs was shown to reduce the CAA burden by 80%; while not producing any evidence of increased cerebral microhemorrhages.

The mechanisms of action of intraperitoneally-administered CpG ODNs relate to the details of the pharmacodynamics of CpG ODNs. In humans, CpG ODNs administered peripherally, but not intravenously, are known to distribute throughout tissues that include mostly liver, kidneys and spleen (Krieg, "Therapeutic Potential of Toll-like Receptor 9 Activation," *Nature Rev Drug Discov* 5:471-84 (2006), which is hereby incorporated by reference in its entirety). In addition, CpG ODNs do not pass through the intact blood-brain-barrier (BBB) (Krieg, "Therapeutic Potential of Toll-like Receptor 9 Activation," *Nature Rev Drug Discov* 5:471-84 (2006); Crack et al., "Toll-like Receptors in the Brain and Their Potential Roles in Neuropathology," *Immunol Cell Biol* 85:476-80 (2007), which are hereby incorporated by reference in their entirety). Direct TLR ligation in microglia is known to enhance their ability to degrade Aβ (Irribaren et al., "CpG-Containing Oligodeoxynucleotide Promotes Microglial Cell Uptake of Amyloid Beta 1-42 Peptide by Up-Regulating the Expression of the G-Protein-Coupled Receptor mFPR2," *FASEB J* 19:2032-34 (2005); Majumdar et al., "Activation of Microglia Acidifies Lysosomes and Leads to Degradation of Alzheimer Amyloid Fibrils," *Mol Biol Cell* 18:1490-96 (2007), which are hereby incorporated by reference in their entirety). Because at early ages and at early stages of AD the BBB is expected to remain intact, direct penetration of CpG ODNs into the brain is unlikely during prophylactic treatment as reported herein. Therefore, direct action of CpG ODN on cells in the brain may not be the mechanism by which this TLR9 agonist reduces Aβ plaque in the CNS.

Early in the disease process, ameliorative mechanisms of TLR9 stimulation may involve direct targets in the periphery. A likely candidate in rodents is peripheral macrophages. Bone marrow-derived macrophages have been found to enter the brain during AD and limit the accumulation of Aβ in plaques; TLR9 is also expressed in this cell type (Stalder et al., "Invasion of Hematopoietic Cells into the Brain of Amyloid Precursor Protein Transgenic Mice," *J Neurosci* 25:11125-32 (2005), which is hereby incorporated by reference in its entirety). The effect of CpG ODN on peripheral macrophages and myeloid and plasmacytoid DCs may be to induce heightened levels of surveillance and activity by these cells, and thus an increased influx into the brain and clearance of Aβ, preventing plaque accumulation. Alternatively, such activation of cells in the periphery may elicit the secretion of cytokines and chemokines that travel to the CNS and act there to induce Aβ clearance by resident microglia, and perhaps by recruiting more macrophages capable of clearing Aβ. That CpG ODN treatment enhances clearance of deposited Aβ through recruitment of peripheral macrophages to the CNS, is supported by increased CD45 immunoreactive microglia around the few remaining plaques in the CpG ODN-treated group (FIG. 9), without associated increases in CD11b immunoreactivity. CD45 labeled microglia have been suggested to have a more likely peripheral origin (Guillemin and Brew, "Microglia, Macrophages, Perivascular Macrophages, and Pericytes: A Review of Function and Identification," *J Leukoc Biol* 75:388-97 (2004), which is hereby incorporated by reference in its entirety). In addition, it is known that CpG ODNs elicit elevated cytokines in the brain (Wagner et al., "Repeated Peripheral Administrations of CpG Oligodeoxynucleotides Lead to Sustained CNS Immune Activation," *Immunopharmacol Immunotoxicol* 29:413-24 (2007), which is hereby incorporated by reference in its entirety).

At later stages of AD, when penetration of CpG ODNs into the CNS may be possible, microglia may be a direct target of the treatment. Mechanisms by which direct TLR ligation on microglia, macrophages and other APCs enhance antigen presentation, and subsequent adaptive immune responses have been described in detail (Blander et al., "On Regulation of Phagosomes Maturation and Antigen Presentation," *Nat Immunol* 7:1029-35 (2006), which is hereby incorporated by reference in its entirety). Such mechanisms appear to involve induction of both phagocytic activation and enhanced antigen presentation (Majundar et al., "Activation of Microglia Acidifies Lysosomes and Leads to Degradation of Alzheimer Amyloid Fibrils," *Mol Biol Cell* 18:1490-96 (2007), which is hereby incorporated by reference in its entirety). If direct activation of microglia does occur in the current model, the clearance of Aβ by microglia is likely very rapid, since at the 17 month time-point at which pathology was evaluated, both microgliosis and Aβ deposition in the CNS is low. This would suggest that after the Aβ is mostly cleared, microgliosis largely subsides.

An alternative possibility, which is not mutually exclusive, is that stimulation of TLR9 by CpG ODN also leads to secondary activation of adaptive immunity with the production of autoantibodies against Aβ. Support for this hypothesis is that there were higher levels of antibodies against Aβ40 in CpG ODN-treated mice at 17 months of age (FIG. 11A). This is not likely to have made a significant impact as at earlier ages when there is active amyloid deposition, however, there were no differences in the levels of anti-Aβ40/42 antibodies in CpG ODN-treated mice versus controls. Also, at no point was there a significant increase among the CpG ODN-treated mice in anti-Aβ42 antibodies. It is Aβ42 that is thought to be the most pathogenic of the Aβ peptides (Walsh et al., "Deciphering the Molecular Basis of Memory Failure in Alzheimer's Disease," *Neuron* 44:181-93 (2004), which is hereby incorporated by reference in its entirety).

The effect of induction of specific TLR signaling has been examined previously in mouse AD models. Knock-out of TLR2 or TLR4 in AD model mice was shown to accelerate Aβ deposition (Tahara et al, "Role of Toll-Like Receptor Signaling in Abeta Uptake and Clearance," *Brain* 129:3006-19 (2006); Richard et al., "Toll-Like Receptor 2 Acts as a Natural Innate Immune Receptor to Clear Amyloid Beta 1-42 and Delay the Cognitive Decline in a Mouse Model of Alzheimer's Disease," *J Neurosci* 28:5784-93 (2008), which are hereby incorporated by reference in their entirety). Accordingly, a single intracranial administration of the TLR4 ligand lipopolysaccharide (LPS) in AD model Tg2576 mice significantly reduces Aβ deposition within 7 days, an effect requiring microglial activation (Herber et al., "Microglial Activation is Required for Abeta Clearance after Intracranial Injection of Lipopolysaccharide in APP Transgenic Mice," *J Neuroimmune Pharmacol* 2:222-231 (2007), which is hereby incorporated by reference in its entirety). Studies in which large doses of the LPS were administer to mice intraperitoneally, however reported deleterious effects, including the exacerbation of amyloid deposition and cognitive declines and/or increased neuroinflammation and neuronal death (Qiao et al., "Neuroinflammation-Induced Acceleration of Amyloid Deposition in the APPV717F Transgenic Mouse," *Eur J Neurosci* 14:474-82 (2001); Cunningham et al., "Central and Systemic Endotoxin Challenges Exacerbate the Local Inflammatory Response and Increase Neuronal Death During Chronic Neurodegeneration," *J Neurosci* 25:9275-84 (2005); Lee et al., "Neuroinflammation Induced by Lipopolysaccharide Causes Cognitive Impairment Through Enhancement of Beta-Amyloid Generation," *J Neuroinflammation* 5:37 (2008), which are hereby incorporated by reference in their entirety). These findings contrast to the results described herein in which peripheral administration of CpG ODNs is clearly beneficial leading to reductions in both amyloid deposition and cognitive decline. Differences between the effects of peripheral LPS and CpG ODNs may be reconciled by the fact that these two TLR agonists trigger different signaling pathways, leading to different cytokine and gene activation profiles (Gao et al., "Regulation of Gene Expression in Mouse Macrophages Stimulated with Bacterial CpG-DNA and Lipopolysaccharides," *J Leukoc Biol* 72:1234-45 (2002), which is hereby incorporated by reference in its entirety). In in vitro studies, it has been observed that even low doses of LPS lead to cytokine responses in macrophages much greater than those observed at high doses of CpG ODNs.

The present invention provides for the stimulation of the TLR9 receptor and thus innate immunity with CpG ODNs as is an effective and apparently non-toxic method to reduce the amyloid burden. This activity has been demonstrated herein in AD model mice. The amyloid reduction is associated with cognitive benefits. This approach has significant implications for future human immunomodulatory approaches to treat and/or prevent AD.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

What is claimed:

1. A method of treating Alzheimer's disease pathology in a subject comprising:
   a) selecting a subject who has Alzheimer's disease pathology and
   b) administering once per month, for at least 10 months, in a range of 1 μg to 10 mg per administration, an oligonucleotide bearing at least one unmethylated class B CpG motif, having a phosphorothioate backbone with one or more CpG dinucleotides, to the selected subject, wherein the administering step is effective to stimulate an innate immune response that reduces brain amyloid-beta depositions, reduces brain aggregated tau depositions, and reduces cerebral vasculature amyloid-beta deposition without causing cerebral microhemorrhage, without toxicity.

2. The method of claim 1, wherein said innate immune system is stimulated by inducing Toll-like receptor signaling in the subject.

3. The method of claim 2, wherein said innate immune system is stimulated by inducing Toll-like receptor 9 signaling in the subject.

4. The method of claim 1, wherein the oligonucleotide has a nucleotide sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, and SEQ ID NO:9.

5. A method of treating cerebral amyloidosis in a subject comprising:
   selecting a subject susceptible to or afflicted with cerebral amyloidosis and
   administering once per month, for at least 10 months, to the selected subject, an agent that stimulates the innate immune system of said subject under conditions effective to treat cerebral amyloidosis, wherein the innate immune system is stimulated by administering an oligonucleotide bearing at least one unmethylated class B CpG motif, having a phosphorothioate backbone with one or more CpG dinucleotides.

6. The method of claim 5, wherein said innate immune system is stimulated by inducing Toll-like receptor signaling.

7. The method of claim 6, wherein said innate immune system is stimulated by inducing Toll-like receptor 9 signaling.

8. The method of claim 5, wherein the oligonucleotide has a nucleotide sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, and SEQ ID NO:9.

9. A method of treating Alzheimer's disease in a subject comprising:
   selecting a subject afflicted with Alzheimer's disease and administering once per month, for at least 10 months, to the selected subject, an agent that stimulates the innate immune system of said subject under conditions effective to treat Alzheimer's disease, wherein the innate immune system is stimulated by administering an oligonucleotide bearing at least one unmethylated class B CpG motif, having a phosphorothioate backbone with one or more CpG dinucleotides.

10. The method of claim 9, wherein said innate immune system is stimulated by inducing Toll-like receptor signaling.

11. The method of claim 10, wherein said innate immune system is stimulated by inducing Toll-like receptor 9 signaling.

12. The method of claim 9, wherein the oligonucleotide has a nucleotide sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, and SEQ ID NO:9.

13. A method of treating Alzheimer's disease pathology in a subject comprising:
   a) selecting a subject who has Alzheimer's disease pathology and
   b) administering once per month, for at least 10 months, in a range of 1 μg to 10 mg per administration, an oligonucleotide bearing at least one unmethylated class B CpG motif, having a phosphorothioate backbone with one or more CpG dinucleotides, to the selected subject, wherein the administering step is effective to stimulate an innate immune response that reduces brain amyloid-beta depositions, reduces brain aggregated tau depositions, and reduces cerebral vasculature amyloid-beta deposition without causing cerebral microhemorrhage, without toxicity, said administering being carried out until AP autoantibody levels in the selected subject are increased at least 2-fold.

14. The method of claim 13, wherein the autoantibody response is towards Aβ40.

15. The method of claim 13, wherein the autoantibody response is towards Aβ42.

16. The method of claim 13 wherein said innate immune system is stimulated by inducing Toll-like receptor signaling in the subject.

17. The method of claim 16, wherein said innate immune system is stimulated by inducing Toll-like receptor 9 signaling in the subject.

18. The method of claim 13, wherein the oligonucleotide has a nucleotide sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, and SEQ ID NO:9.

* * * * *

UNITED STATES PATENT AND TRADEMARK OFFICE
CERTIFICATE OF CORRECTION

PATENT NO.         : 10,960,019 B2
APPLICATION NO.    : 16/458966
DATED              : March 30, 2021
INVENTOR(S)        : Wisniewski et al.

Page 1 of 1

It is certified that error appears in the above-identified patent and that said Letters Patent is hereby corrected as shown below:

In the Claims

Column 28, Line 66 in Claim 13, delete "AP autoantibody levels" and insert in its place --Aβ autoantibody levels--

Signed and Sealed this
Fifteenth Day of June, 2021

Drew Hirshfeld
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 9

<210> SEQ ID NO 1
<211> LENGTH: 20
<212> TYPE: DNA
<213> ORGANISM: Artificial
<220> FEATURE:
<223> OTHER INFORMATION: ODN 1826

```
<400> SEQUENCE: 1
tccatgacgt tcctgacgtt                                                    20

<210> SEQ ID NO 2
<211> LENGTH: 20
<212> TYPE: DNA
<213> ORGANISM: Artificial
<220> FEATURE:
<223> OTHER INFORMATION: ODN 1631

<400> SEQUENCE: 2
cgcgcgcgcg cgcgcgcgcg                                                    20

<210> SEQ ID NO 3
<211> LENGTH: 20
<212> TYPE: DNA
<213> ORGANISM: Artificial
<220> FEATURE:
<223> OTHER INFORMATION: ODN 1984

<400> SEQUENCE: 3
tccatgccgt tcctgccgtt                                                    20

<210> SEQ ID NO 4
<211> LENGTH: 20
<212> TYPE: DNA
<213> ORGANISM: Artificial
<220> FEATURE:
<223> OTHER INFORMATION: ODN 2010

<400> SEQUENCE: 4
gcggcgggcg gcgcgcgccc                                                    20

<210> SEQ ID NO 5
<211> LENGTH: 17
<212> TYPE: DNA
<213> ORGANISM: Artificial
<220> FEATURE:
<223> OTHER INFORMATION: CpG 1758

<400> SEQUENCE: 5
ctcccagcgt gcgccat                                                       17

<210> SEQ ID NO 6
<211> LENGTH: 24
<212> TYPE: DNA
<213> ORGANISM: Artificial
<220> FEATURE:
<223> OTHER INFORMATION: CpG 2006

<400> SEQUENCE: 6
tcgtcgtttt gtcgttttgt cgtt                                               24

<210> SEQ ID NO 7
<211> LENGTH: 20
<212> TYPE: DNA
<213> ORGANISM: Artificial
<220> FEATURE:
<223> OTHER INFORMATION: CpG 1668

<400> SEQUENCE: 7
tccatgacgt tcctgatgct                                                    20

<210> SEQ ID NO 8
```

-continued

```
<211> LENGTH: 24
<212> TYPE: DNA
<213> ORGANISM: Artificial
<220> FEATURE:
<223> OTHER INFORMATION: CpG 7909

<400> SEQUENCE: 8
tcgtcgtttt gtcgttttgt cgtt                                          24

<210> SEQ ID NO 9
<211> LENGTH: 22
<212> TYPE: DNA
<213> ORGANISM: Artificial
<220> FEATURE:
<223> OTHER INFORMATION: ODN 1018 ISS

<400> SEQUENCE: 9
tgactgtgaa cgttcgagat ga                                            22
```